US009044566B2

(12) United States Patent
Wickham et al.

(10) Patent No.: US 9,044,566 B2
(45) Date of Patent: Jun. 2, 2015

(54) ADVANCED SUPPORTED LIQUID MEMBRANES FOR CARBON DIOXIDE CONTROL IN EXTRAVEHICULAR ACTIVITY APPLICATIONS

(71) Applicant: Reaction Systems, LLC, Golden, CO (US)

(72) Inventors: David T. Wickham, Lafayette, CO (US); Kevin J. Gleason, Lafayette, CO (US); Scott W. Cowley, Lakewood, CO (US)

(73) Assignee: Reaction Systems, LLC, Golden, CO (US)

( * ) Notice: Subject to any disclaimer, the term of this patent is extended or adjusted under 35 U.S.C. 154(b) by 0 days.

(21) Appl. No.: 14/195,615

(22) Filed: Mar. 3, 2014

(65) Prior Publication Data

US 2014/0283839 A1    Sep. 25, 2014

Related U.S. Application Data

(60) Provisional application No. 61/771,790, filed on Mar. 1, 2013, provisional application No. 61/846,068, filed on Jul. 14, 2013.

(51) Int. Cl.
| | | |
|---|---|---|
| *B01D 53/22* | (2006.01) | |
| *A61M 16/22* | (2006.01) | |
| *A62B 19/02* | (2006.01) | |

(Continued)

(52) U.S. Cl.
CPC .............. *A61M 16/22* (2013.01); *A62B 19/02* (2013.01); *B01D 2257/504* (2013.01); *Y02C 10/10* (2013.01); *B01D 53/228* (2013.01); *B01D 53/00* (2013.01); *B64D 13/00* (2013.01); *C01B 31/20* (2013.01); *A62B 19/00* (2013.01); *B64G 9/00* (2013.01)

(58) Field of Classification Search
CPC ................ Y02C 10/10; B01D 53/228; B01D 2257/504; A61M 16/22; A62B 19/02
USPC ............................... 95/45, 51, 52; 96/5, 8, 10
See application file for complete search history.

(56) References Cited

U.S. PATENT DOCUMENTS 6,579,343 B2 *  6/2003  Brennecke et al. ............... 95/51
6,958,085 B1 * 10/2005  Parrish .............................. 95/44

(Continued)

OTHER PUBLICATIONS

Advantec "Membrane Filters" Jun. 16, 2012 <https://web.archive.org/web/20120616164442/http://www.advantecmfs.com/catalog/filt/membrane.pdf>.*

(Continued)

*Primary Examiner* — Jason M Greene
*Assistant Examiner* — Anthony Shumate
(74) *Attorney, Agent, or Firm* — Sheridan Law, LLC

(57) ABSTRACT

There is disclosed a portable life support system with a component for removal of at least one selected gas. In an embodiment, the system includes a supported liquid membrane having a first side and a second side in opposition to one another, the first side configured for disposition toward an astronaut and the second side configured for disposition toward a vacuum atmosphere. The system further includes an ionic liquid disposed between the first side and the second side of the supported liquid membrane, the ionic liquid configured for removal of at least one selected gas from a region housing the astronaut adjacent the first side of the supported liquid membrane to the vacuum atmosphere adjacent the second side of the supported liquid membrane. Other embodiments are also disclosed.

21 Claims, 24 Drawing Sheets

(51) Int. Cl.
| | |
|---|---|
| *B01D 53/00* | (2006.01) |
| *B64D 13/00* | (2006.01) |
| *C01B 31/20* | (2006.01) |
| *B64G 99/00* | (2009.01) |
| *A62B 19/00* | (2006.01) |

(56) References Cited

U.S. PATENT DOCUMENTS

| | | | |
|---|---|---|---|
| 7,833,643 B2* | 11/2010 | Angell et al. | 429/492 |
| 7,938,890 B2* | 5/2011 | Littau et al. | 96/4 |
| 7,938,891 B2* | 5/2011 | Littau | 96/5 |
| 7,938,892 B2* | 5/2011 | Littau | 96/5 |
| 7,943,543 B1* | 5/2011 | Liu et al. | 502/4 |
| 8,026,018 B2* | 9/2011 | Ohma et al. | 429/508 |
| 8,277,691 B2* | 10/2012 | Lu | 252/511 |
| 8,394,181 B2* | 3/2013 | Ishida et al. | 96/4 |
| 8,449,652 B2* | 5/2013 | Radosz et al. | 95/51 |
| 8,715,392 B2* | 5/2014 | Liu | 95/51 |
| 2003/0154857 A1* | 8/2003 | Murdoch | 95/51 |
| 2006/0034035 A1* | 2/2006 | Maruo et al. | 361/502 |
| 2007/0122675 A1* | 5/2007 | Angell et al. | 429/33 |
| 2008/0041791 A1* | 2/2008 | Cooper et al. | 210/695 |
| 2009/0104507 A1* | 4/2009 | Ohma et al. | 429/35 |
| 2010/0132559 A1* | 6/2010 | Ishida et al. | 96/5 |
| 2011/0052466 A1* | 3/2011 | Liu | 423/230 |
| 2011/0236295 A1* | 9/2011 | Anderson et al. | 423/437.1 |
| 2012/0100461 A1* | 4/2012 | Iden et al. | 429/516 |
| 2014/0238235 A1* | 8/2014 | Liu et al. | 95/52 |
| 2014/0272734 A1* | 9/2014 | Braun et al. | 431/11 |

OTHER PUBLICATIONS

Petra et al. "Ionic Liquids: Applications and Perspectives" "Application of Ionic Liquids in Membrane Separation Processes" pp. 561-586 Feb. 2011 <http://cdn.intechopen.com/pdfs-wm/13743.pdf>.*

Scovazzo et al. "Supported Ionic Liquid Membranes and Facilitated Ionic Liquid Membranes" p. 69-87 ACS Symposium Series; American Chemical Society: Washington, DC, 2002. Publication Date: Jul. 25, 2002<http://pubs.acs.org/doi/pdf/10.1021/bk-2002-0818.ch006>.*

Barta, Daniel J., et al., "Life Support System Technology Development Supporting Human Space Exploration", NASA Johnson Space Center, 9 pp, 2008-01-2185.

Barta, Daniel J., et al., "Development of Life Support System Technologies for Human Lunar Missions", NASA Johnson Space Center, SAE International, 8 pp, 2009-01-2483.

Dillon, Paul, et al., "Flexible Packaging Concept for a Space Portable Life Support Subsystem", SAE International, 12, pp.

Hanioka, Shoji, et al., "CO2 Separation Facilitated by Task-Specific Ionic Liquids Using a Supported Liquid Membrane", Journal of Membrane Science, vol. 314, pp. 1-4, 2008.

Iacomini, Christine, et al., "Demonstration of Metabolic Heat Regenerated Temperature Swing Adsorption Technology", SAE International, 2007, 11 pp.

Iacomini, Christine S., et al., "Testing, Modeling and System Impact of Metabolic Heat Regenerated Temperature Swing Adsorption", SAE International, 2008, 12 pp, 2008-01-2116.

Iacomini, Christine S., et al., "PLSS Scale Demonstration of MTSA Temperature Swing Adsorption Bed Concept for CO2 Removal/Rejection", SAE International, 2009, 11 pp.

Iacomini, Christine, et al., "Transient Modeling and Analysis of a Metabolic Heat-Regenerated Temperature Swing Adsorption System for a Portable Life Support System", 40th International Conference on Environmental Systems, The American Institute of Aeronautics and Astronauts, Inc., 2010, 16 pp.

Koscielniak, Agnieszka A., et al., "Development and Testing of a Metabolic Workload Measuring System for Space Suits", SAE International, 2007, 13 pp.

Papale, William, et al., Development Status of the Carbon Dioxide and Moisture Removal Amine Swing-Bed Systems (CAMRAS) Hamilton Sundstrand Space Systems International, Inc., Published by SAE International, 2009, 5 pp.

Papale, William, et al., "Development Status of an EVA-Sized Cycling Amine Bed System for Spacesuit Carbon Dioxide and Humidity Removal", Hamilton Sundstrand Space Systems International, Inc., Published by SAE International, 2007, 5 pp.

Watts, Carly, et al., "Space Suit Portable Life Support System Test Bed (PLSS 1.0) Development and Testing" 42nd International Conference on Environmental Systems, Jul. 15-19, 2012, 34 pp.

Wickham, David T., et al., "Advanced Supported Liquid Membranes for CO2 Control in Extravehicular Activity Applications", 43rd International Conference on Environmental Systems (ICES), Jul. 14-18, 2013, 24 pp.

* cited by examiner

ADVANCED SUPPORTED LIQUID MEMBRANES FOR CARBON DIOXIDE CONTROL IN EXTRAVEHICULAR ACTIVITY APPLICATIONS

REFERENCE TO PENDING PRIOR PATENT APPLICATION

This application claims the benefit under 35 U.S.C. 119 (e) of U.S. Provisional Patent Application No. 61/771,790, filed Mar. 1, 2013 for ADVANCED SUPPORTED LIQUID MEMBRANES FOR CARBON DIOXIDE CONTROL IN EXTRAVEHICULAR ACTIVITY APPLICATIONS and U.S. Patent Application Ser. No. 61/846,068, filed Jul. 14, 2013 for ADVANCED SUPPORTED LIQUID MEMBRANES FOR CARBON DIOXIDE CONTROL IN EXTRAVEHICULAR ACTIVITY APPLICATIONS.

GOVERNMENT LICENSE RIGHTS

This invention was made with government support under contract number NNX12CA65C awarded by NASA. The government has certain rights in the invention.

BACKGROUND

NASA has a clear need to develop new technology in support of its future mission objectives, whether they are beyond low earth orbit (BLEO) missions, the development of Lunar outposts, or the eventual exploration of Mars. As these missions develop, it is anticipated that crew members will spend extended time outside of space craft and established habitats, and therefore the agency is focused on the development of new, robust, lightweight life support systems for extra-vehicular activity (EVA). One area that is critical to life support systems is the control of $CO_2$ and new space suits must be able to accommodate longer EVAs without increasing the size or weight of the primary life support system (PLSS). Since the lifetime of the sorbent currently used for $CO_2$ control can be a limiting factor in EVA duration, the development of lighter, simpler, and reliable methods for $CO_2$ control is a primary need to support advanced exploration. Indeed, previous works classify the development of advanced technologies for $CO_2$ control as "critical" to NASA's current needs. (Barta, D. J. and M. K Ewert, "Development of Life Support System Technologies for Human Space Exploration", SAE Paper 2009-01-2483, 39th Int. Conf. on Environmental Systems, Savannah Ga., 2009. Barta, D. J., M. K Ewert, M. S. Anderson, and J. McQuillan, "Life Support System Technology Development Supporting Human Space Exploration", SAE Paper 2008-01-2185, 38th International Conference on Environmental Systems, San Francisco Calif. 2008.)

The rate of $CO_2$ generation varies with the metabolic rate of the crew member. Recent studies of $CO_2$ control technology have been carried out in which the $CO_2$ injection rates were varied to match simulated metabolic rates. The average $CO_2$ generation rate was determined to be 0.093 g/h per Btu/h of metabolic rate of activity (Wickham, D. T., Gleason, K. J., Cowley, S. C., Engel, J. R., and Chullen, C., "Advanced Supported Liquid Membranes for $CO_2$ Control in EVA Applications", SAE Paper 2013-01-3212, 43rd International Conference on Environmental Systems, Vail Colo., 2013). Assuming that the metabolic rate over an EVA is approximately 1000 Btu/h, then the average rate of $CO_2$ production is 93 g/h. In addition, based on recent findings regarding the effect that $CO_2$ has on decision making capability, NASA also has a current interest in reducing the maximum allowable CO2 concentration in the suit from 7.6 mm Hg to 2.8 mm Hg. (Wickham, D. T., Gleason, K. J., Cowley, S. C., Engel, J. R., and Chullen, C., "Advanced Supported Liquid Membranes for $CO_2$ Control in EVA Applications", SAE Paper 2013-3307, 43rd International Conference on Environmental Systems, Vail Colo., 2013.) Thus, in order to carry out EVA operations safely, the $CO_2$ control system must be sized to handle at least average production rates for the duration of the EVA, which likely will last in excess of eight hours.

Current Methods for $CO_2$ Control for EVA and on Space Craft

Currently, the Metox sorbent system, designed and constructed by Hamilton Sundstrand, is being used for $CO_2$ control during EVA. The Metox employs a silver oxide sorbent, which reacts with $CO_2$ at low temperature to produce silver carbonate. It is designed to maintain the $CO_2$ pressure of less than 7.6 mm Hg at metabolic generation rate of up to 403 kcal/h. During an EVA operation, the silver is gradually converted to the metal carbonate and once all of the oxide has been converted, the canister is no longer effective. After the EVA, the canister is placed in a specially designed oven on board the spacecraft. It is then heated in a flow of air to about 200° C. causing the carbonate to decompose back into the oxide, regenerating the activity of the Metox for the next mission. Since the Metox canister cannot be regenerated during the EVA, its capacity can be a limiting factor in the mission duration and the only way to increase EVA time is to increase the size and weight of the canister.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is provided a portable life support system with a component for removal of at least one selected gas, the system comprising a supported liquid membrane having a first side and a second side in opposition to one another, the first side configured for disposition toward an astronaut and the second side configured for disposition toward a vacuum atmosphere; and an ionic liquid disposed between the first side and the second side of the supported liquid membrane, the ionic liquid configured for removal of at least one selected gas from a region housing the astronaut adjacent the first side of the supported liquid membrane to the vacuum atmosphere adjacent the second side of the supported liquid membrane.

In another embodiment, there is provided a method of removal of at least one selected gas from a portable life support system, the method comprising:

providing the portable life support system with a component for removal of at least one selected gas, the system comprising a supported liquid membrane having a first side and a second side in opposition to one another, the first side configured for disposition toward an astronaut and the second side configured for disposition toward a vacuum atmosphere; and an ionic liquid disposed between the first side and the second side of the supported liquid membrane, the ionic liquid configured for removal of at least one selected gas from a region housing the astronaut adjacent the first side of the supported liquid membrane to the vacuum atmosphere adjacent the second side of the supported liquid membrane; producing the selected gas within the system on the first side of the supported liquid membrane; and removing the selected gas from the system on the second side of the supported liquid membrane.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1:
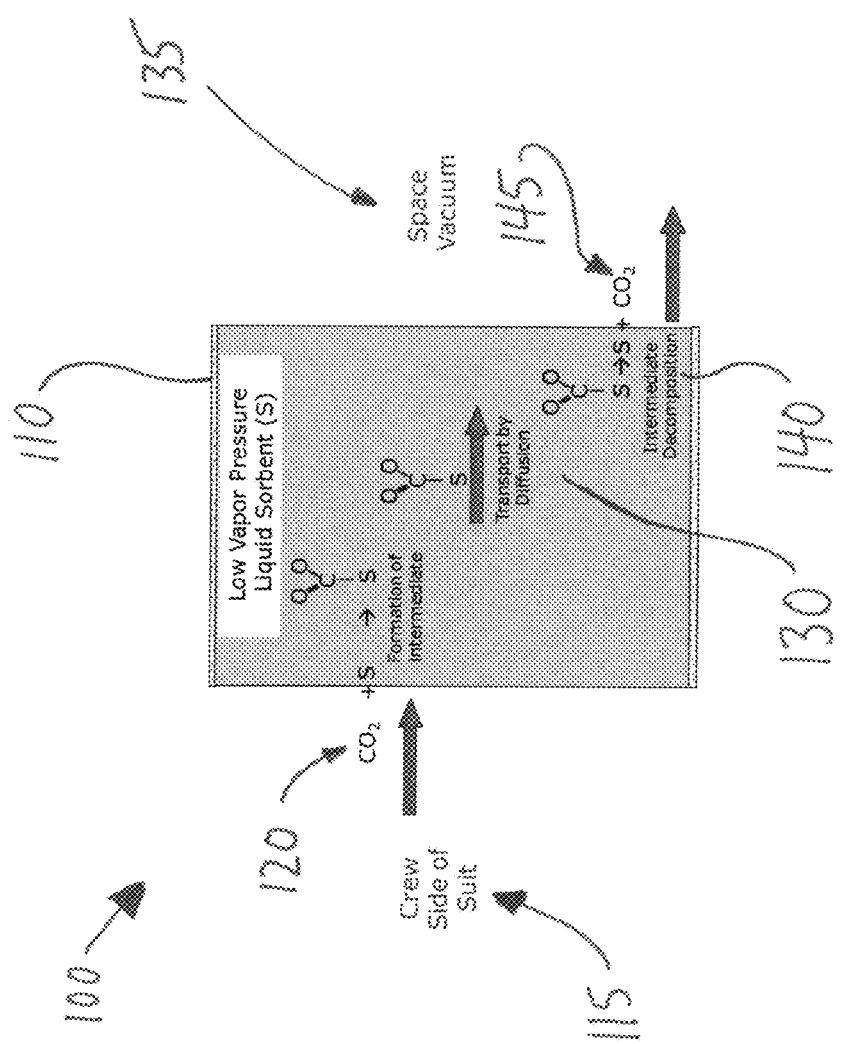
FIG. 1 is a schematic illustration of facilitated $CO_2$ transport within a membrane pore.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

The most common approach to developing new methods for $CO_2$ removal in EVA applications is the use of rapidly regenerable sorbent systems, which are alternately used to remove $CO_2$ and then taken off line for regeneration. This strategy offers the benefit of smaller adsorption beds and life times limited only by the number of times the sorbent can be loaded and regenerated. However, the trade-off is the increased complexity, size and weight, power consumption, and finally the potential failures associated with the hardware required to carry out the regeneration. Instead of storing the regeneration hardware in the spacecraft as is done now, the equipment must now be integrated into the PLSS.

Sorbent regeneration can be accomplished either by simply reducing the partial pressure of $CO_2$ (pressure swing) or by heating the sorbent (temperature swing) under reduced $CO_2$ partial pressure. Changing the temperature of the bed requires a source of heat (or cooling) which complicates the hardware, and because sorbents typically consist of high surface area solids, their thermal conductivities are usually quite low, which increases heating and cooling times. Currently, there are a number of different approaches under investigation. Although each has its strong points, none of these technologies meets all of the demands imposed by advanced space exploration. Recent work describes a rapid-cycling amine, designated SA9T. (Papale, W. and H. L. Paul, "Development Status of an EVA-sized Cycling Amine Bed System for Spacesuit Carbon Dioxide and Humidity Removal", SAE Paper 2007-01-3272, 37th *International Conference on Environmental Systems*, Chicago Ill., 2007. Papale, W., T. Nalette, and J. Sweterlitsch, "Development Status of the Carbon Dioxide and Moisture Removal Amine Swing-Bed System (CAMRAS)", SAE Paper 2009-01-2441, 39th *International Conference on Environmental Systems*, Savannah Ga., 2009.) Approximately 715 $cm^3$ of the sorbent was exposed to $CO_2$ flows ranging from about 30 g/h (representing an "at rest" activity level) up to 174 g/h (a high activity level). The results indicated that the maximum allowable cycle time decreased as the $CO_2$ input flow rate increased. For example at a $CO_2$ flow rate of 90 g/h the cycle time was about 5 min, while at 174 g/h, the cycle time was only about 1 minute. Unfortunately, the shorter cycle times increase the oxygen that would be lost to space during regeneration. At the highest $CO_2$ flow, the oxygen losses were over 5 g/h, which represents a significant oxygen loss rate.

Temperature swing systems are also being investigated. Recent work has evaluated the use of metabolic heat to regenerate the sorbent during EVA. (Iacomini, C., A. Powers, and H. L. Paul, "PLSS Scale Demonstration of MTSA Temperature Swing Adsorption Bed Concept for CO2 Removal/Rejection", SAE Paper 2009-01-2388, 39th *International Con-* ference on *Environmental Systems*, Savannah, Ga., 2009. Iacomini, C., A. Powers, G. Speight, S. Padilla, and H. L. Paul, "Transient Modeling and Analysis of a Metabolic Heat-Regenerated Temperature Swing Adsorption System for a Portable Life Support System", AIAA Paper 2010-6013, *40th International Conference on Environmental Systems*, Barcelona Spain, 2010. Iacomini, C., A. Powers, J. Dunham, K. Straub-Lopez, G. Anderson, T. MacCallum, and H. L. Paul, "Demonstration of Metabolic Heat Regenerated Temperature Swing Adsorption Technology", SAE Paper 2007-01-3274, *37th International Conference on Environmental Systems*, Chicago Ill., 2007. Iacomini, C., A. Powers, M. Lewis, G. Waguespack, B. Congor, and H. L. Paul, "Model Calibration Experiments in Support of Metabolic Heat Regenerated Temperature Swing Adsorption Technology", SAE Paper 2008-01-2116, *38th International Conference on Environmental Systems*, San Francisco, Calif., 2008.) In this approach, liquid $CO_2$ is used to cool a commercial sorbent to 210 K for adsorption and metabolic heat generated by the crew member to raise the bed temperature to about 280 K for regeneration. In recent work, the difficulty of applying temperature swing absorption to sorbent materials that have inherently low thermal conductivity in a packed bed configuration is described. (Iacomini, C., A. Powers, and H. L. Paul, "PLSS Scale Demonstration of MTSA Temperature Swing Adsorption Bed Concept for CO2 Removal/Rejection", SAE Paper 2009-01-2388, *39th International Conference on Environmental Systems*, Savannah, Ga., 2009.) To improve thermal conductivity, thin layers of the sorbent were coated on a reticulated aluminum foam. The results indicated that the sorbent loadings in this configuration were lower than in the packed bed and the authors attributed this to mass transfer limitations.

Although much work has been conducted to identify methods to control $CO_2$ in EVA and much progress has been made, a simple, reliable approach that substantially extends mission times has not yet been identified. The use of sorbents that rapidly cycle between adsorption and regenerations requires additional "on back" hardware, adding size, weight, complexity, increasing the use of electrical power, and finally and perhaps most important, reducing the system reliability.

Criteria for $CO_2$ Control with a Liquid Membrane

Probably the simplest way to control $CO_2$ would be with a membrane that is selective for $CO_2$ over $O_2$. A membrane has several advantages over the other methods of $CO_2$ control discussed above. It provides a continuous system with no inherent limit on the amount of $CO_2$ removed, it would be very simple requiring very little hardware or moving parts, and it would have low power demand and should be very reliable.

However, successful application of a membrane has some challenges. First the selectivity of the membrane for $CO_2$ over $O_2$ must be very high. Estimates of required $CO_2$ permeance are based on the volume limit of 0.25 ft3, which is the size of the rapid cycle amine. Seader and Henley indicate that hollow fiber modules, can produce surface area to volume ratios from 500 to 9000 $m^2/m^3$. Using an intermediate value of 7000 $m^2/m^3$ (or 198 $m^2/ft^3$), it was concluded that a module that has a volume of 0.25 $ft^3$ could contain a total surface area of 49.6 $m^2$ (496,000 $cm^2$). The module needs to control at least the average $CO_2$ production rate of 93 g/h (or 14.4 scc $CO_2$/s) and therefore the required $CO_2$ flux through the membrane is 3.12E-5 $scc/(cm^2 s)$. Finally, with a maximum allowable $CO_2$ partial pressure of 0.30 cm Hg (3.0 mm Hg) in the suit, the flux and be converted to a permeance of 1.04E-5 $scc/(cm^2$ s cm Hg).

Finally, the membrane must have a low enough $O_2$ permeance to prevent excessive $O_2$ losses. Although achieving a zero $O_2$ loss rate is desirable, a more reasonable first approximation is to set the maximum acceptable $O_2$ loss rate at the same value that is lost through leakage in the suit. Watts et al. indicate that suit leakage rates can reach 4.2 g/h (0.90 scc/s) and this rate is also within the range of $O_2$ losses reported for the RCA. Therefore, setting the maximum loss rate in a SLM at 4.2 g/h is a reasonable starting point. (Watts, C., Campbell, C., Vogel, M, and Conger, B., "Space Suit Portable Life Support System Test Bed (PLSS 1.0) Development and Testing", AIAA 2012-3456, *42nd International Conference on Environmental Systems*, San Diego, Calif., 2012.) With a membrane area of 496,000 $cm^2$ and an exposure pressure of 22.8 cm Hg (0.3 atm), an $O_2$ loss rate of 4.2 g/h would be produced with an $O_2$ permeance of 7.89E-8 ($scc/cm^2$s cm Hg). Thus the $CO_2/O_2$ selectivity is [1.04E-5 $scc/(cm^2$ s cm Hg)/7.89E-8 $scc/(cm^2$ s cm Hg)] or 1300.

Conventional polymeric gas separation membranes have not been able to meet the needs of the PLSS because of the inherent trade-off between selectivity and permeability of polymeric materials.

A better approach may be the development of a supported (or immobilized) liquid membrane (SLM) where the chemistry of the liquid immobilized within the membrane may be tailored to achieve the desired selective absorption of $CO_2$ over $O_2$ on the crew side of the membrane and still allow $CO_2$ to desorb when exposed to space vacuum. In this application, the immobilized liquid may form a metastable complex with $CO_2$ on the crew side of the membrane. The complex diffuses through the liquid contained in the membrane pores, ultimately reaching the vacuum side of the membrane, where the absence of gas phase $CO_2$ shifts the equilibrium resulting in the decomposition of the metastable complex, the release of the $CO_2$ and the regeneration of the sorbent. SLMs effectively combine the absorption and stripping processes into one unit operation.

To achieve selective transport, the liquid reagent material should meet several criteria. First, the affinity between $CO_2$ and the carrier may be configured higher than for the other compounds contained in the exhaled air. Next, because the membrane operates at constant temperature, the liquid should be fully regenerable by exposure to space vacuum and not require any temperature change to increase capacity. Third, the liquid should have low viscosity so the complex can diffuse quickly from one side of the membrane to the other. Fourth, and perhaps most important, the liquid reactant should be configured with effectively zero vapor pressure so it is not lost by evaporation to space.

Amines are commonly used to absorb $CO_2$ out of industrial gas streams. Most amines for $CO_2$ control include an alcohol or other polar functional group to reduce volatility. Unfortunately, the vapor pressure of conventional amines is too high and they would rapidly evaporate when exposed to space vacuum. However, ionic liquids, a relatively new class of compounds has the potential to perform very effectively in this application. Ionic liquids are relatively lightweight hydrocarbons that typically consist of cations and anions and as a result they have effectively zero vapor pressure. Therefore, a series of ionic liquids was prepared that contain amine functional groups giving them good affinity for $CO_2$ and measured their performance in a supported liquid membrane.

A schematic diagram 100 of an exemplary facilitate $CO_2$ transport process is shown in FIG. 1. A novel sorbent group 105 is immobilized within the pores of a microporous membrane 110. On the crew member side 115 of the membrane 110, $CO_2$ 120 contacts the sorbent group 105 forming the metastable complex 125. Thus, on the high pressure side 115 of the membrane 110, the concentration of the complex 125 increases to that predicted by equilibrium. The complex 125 then diffuses 130 to the low pressure side of the membrane 135, which is exposed to space vacuum. Since the $CO_2$ partial pressure is effectively zero, the complex formation reaction reverses 140, causing gas phase $CO_2$ 145 to be produced, which is then vented to space. At the same time, this reaction also regenerates the liquid sorbent. This approach will produce a supported liquid membrane that can be used to control $CO_2$ in EVA applications.

Experimental Methods
Compounds Prepared

Figure 2:
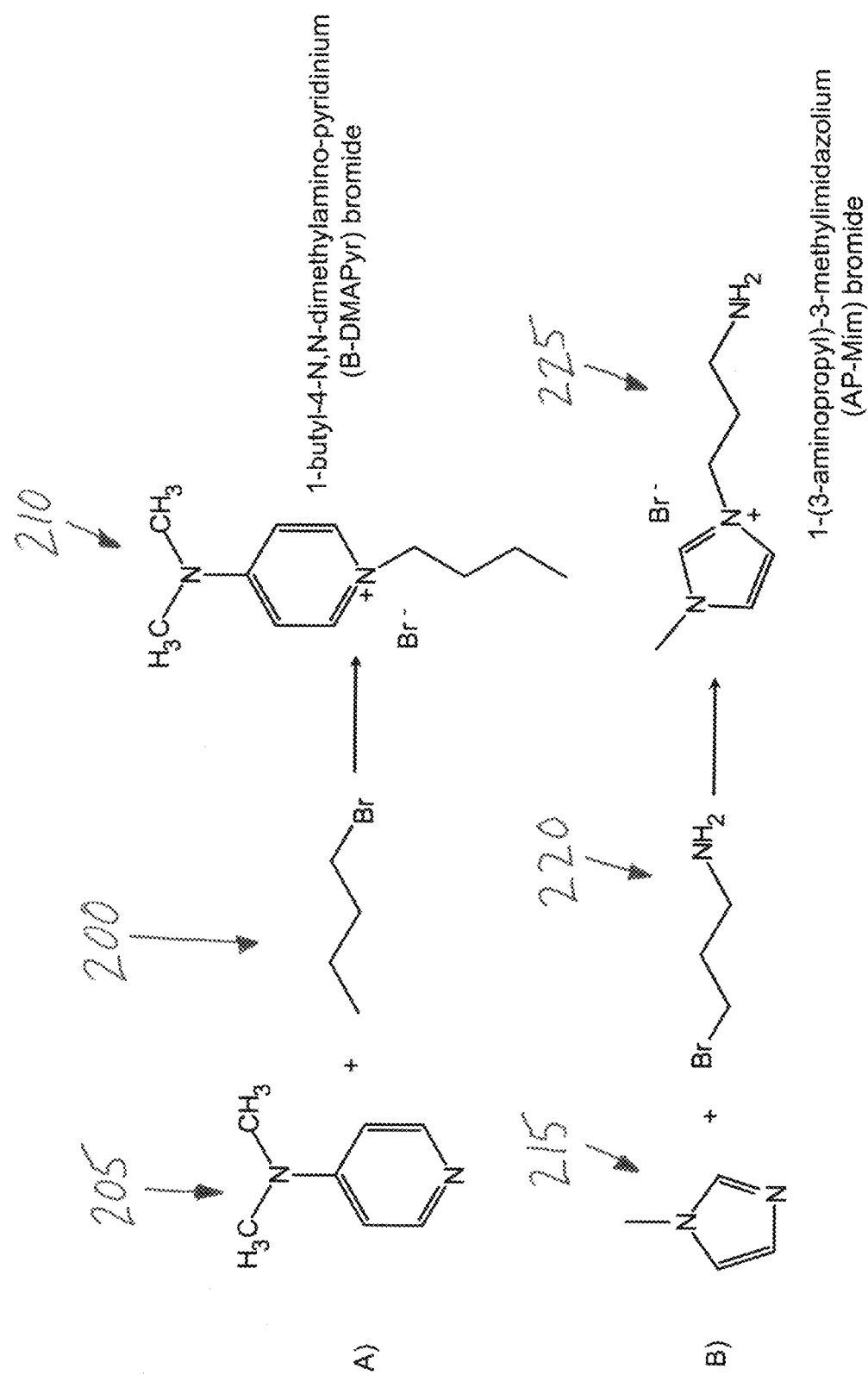
FIG. 2 illustrates simplified synthetic schemes for the ionic liquid compounds produced.

The sorbents may include ionic liquids functionalized with an amine group. Ionic liquids are relatively low molecular weight hydrocarbon-based compounds that can have low viscosity and have effectively zero vapor pressure. Thus, these sorbents are excellent choices for use in a supported liquid membrane where one side will be exposed to space vacuum. In exemplary embodiments provided herein, the results are obtained with two compounds, one containing a tertiary amine functional group, 1-butyl-4-N,N-(dimethylamino) pyridinium or B-DMAPyr 210, and one containing a primary amine function group, 1-(3-aminopropyl)-3-methylimidazolium or AP-Mim 225. The simplified synthetic schemes are shown in FIG. 2. To produce the tertiary containing ionic liquid 1-bromobutane 200 was reacted with 4-dimethylaminopyridin 205 (FIG. 2A). To produce the primary amine containing ionic liquid 1-methylimidazole 215 was reacted with 3-bromopropylamine 220 (FIG. 2B). When the alkyl group bonds with the nitrogen atom in either the pyridinium or imidazolium rings, it results in a nitrogen atom with four bonds, resulting in a positive charge on the ion. A variety of anions can be incorporated into the liquid by ion exchange. The choice of the anion can have a substantial effect on the viscosity and the melting point of the liquid. In these tests both ionic liquids were exchanged with the bis(trifluoromethanesulfonyl)amide anion ($Tf_2N$) to reduce viscosity. After completing the synthetic procedure, the final step is to remove the solvent leaving the very low vapor pressure sorbent.

Sorbent Characterization by and NMR

Once the sorbents were prepared, the sorbents were characterized by Nuclear Magnetic Resonance (NMR) spectroscopy. To carry out this work, a JEOL NMR Model ECA-500, 500 MHz was used for NMR characterization, with $D_2O$ or $CDCl_3$ as the solvents.

Membrane Permeation Rate Measurements
Permeance Testing
Single Gas Test Rig

Figure 3:
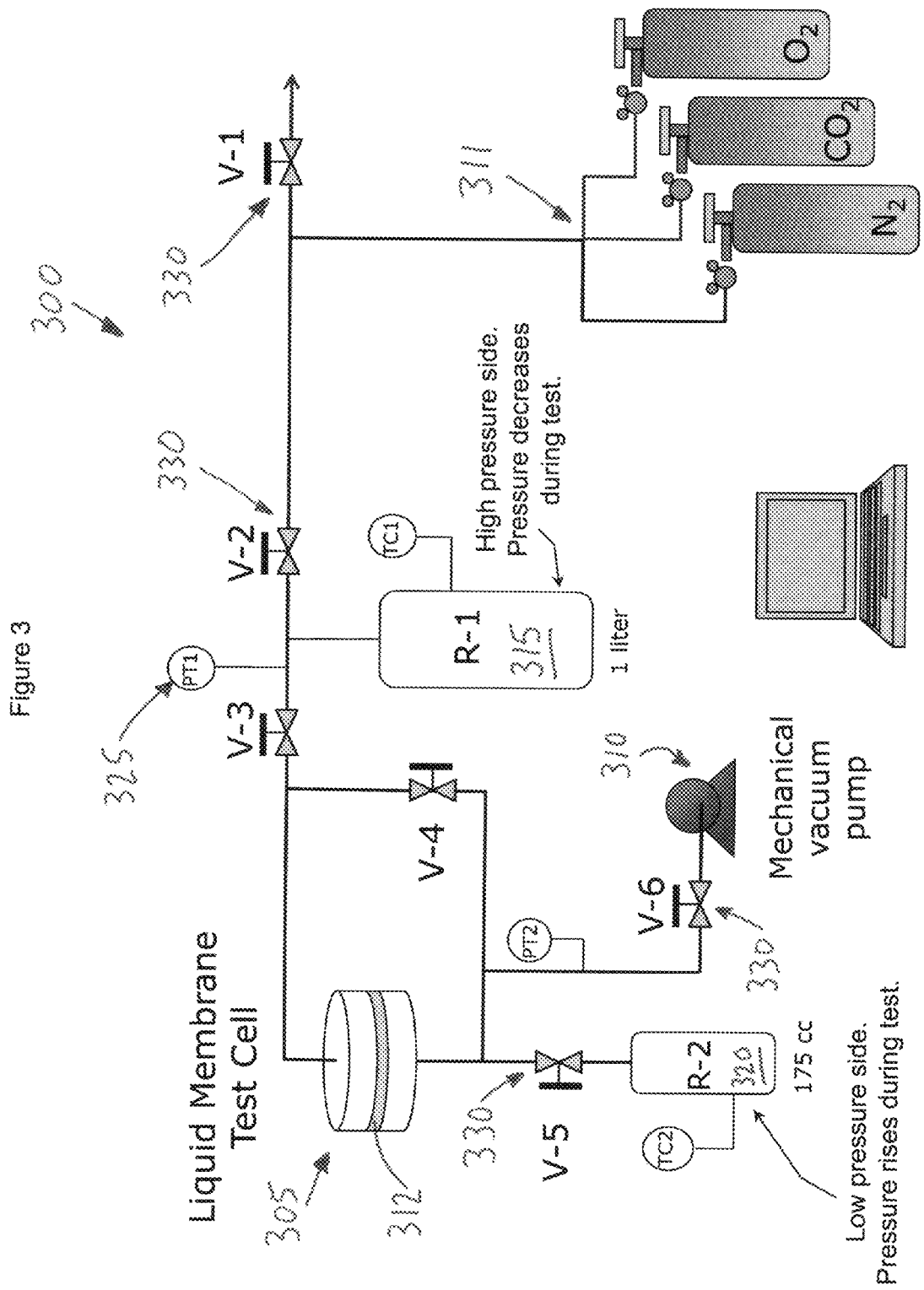
FIG. 3 illustrates an exemplary embodiment of a liquid membrane permeation system.

After completing the $CO_2$ uptake measurements, tests to measure the permeation rate of $CO_2$ through membranes containing the novel sorbents were carried out. A schematic of the membrane test rig 300 is shown in FIG. 3. The system may include the membrane housing 305, a mechanical pump 310 capable of reaching pressures down to 20 mtorr, and a manifold 311 that is used to expose the membrane 312 to $CO_2$ or $O_2$ and monitor the gas flow through the membrane. The manifold includes a one liter reservoir (R-1) 315, a 175 cc reservoir (R-2) 320, pressure transducers 325 on the high and low pressure side of the membrane 312, and valves 330 that permit the control of pressure in various sections of the system. The system may include LabVIEW-brand software and National Instruments-band hardware for control and data acquisition.

The membrane housing consists of two aluminum flanges with flow passages machined into each. The heights of the support were adjusted to accommodate a stainless steel mesh that supports the liquid-impregnated membrane on the low-pressure side. Two O-rings fit in the shallow recess, machined in the flange around the flow path. The inner O-ring seals the membrane to the flange preventing bypass of the challenge compound. The outside O-ring is pressed between the upper and lower flange outside of the membrane and prevents leaks into the system that could come in from the outer edge of the membrane.

To conduct each test, a membrane impregnated with approximately one gram of sorbent was placed on top of the stainless steel mesh on the bottom flange. The top flange was placed over the membrane and secured with bolts and the membrane assembly was connected to the system manifold. After leak checking, the entire system was evacuated to 20 mtorr. Reservoir R-1 was then isolated from the vacuum pump and charged with 0.2 atm of either $CO_2$ or $O_2$. The low pressure side of the manifold was then isolated from the vacuum pump and the high pressure manifold by closing valves V-4 and V-6. Finally the membrane was opened to R-1 by opening valve V-3. The pressures in the manifolds on both sides of the membrane were then monitored.

Mixed Gas Test Rig

Figure 4:
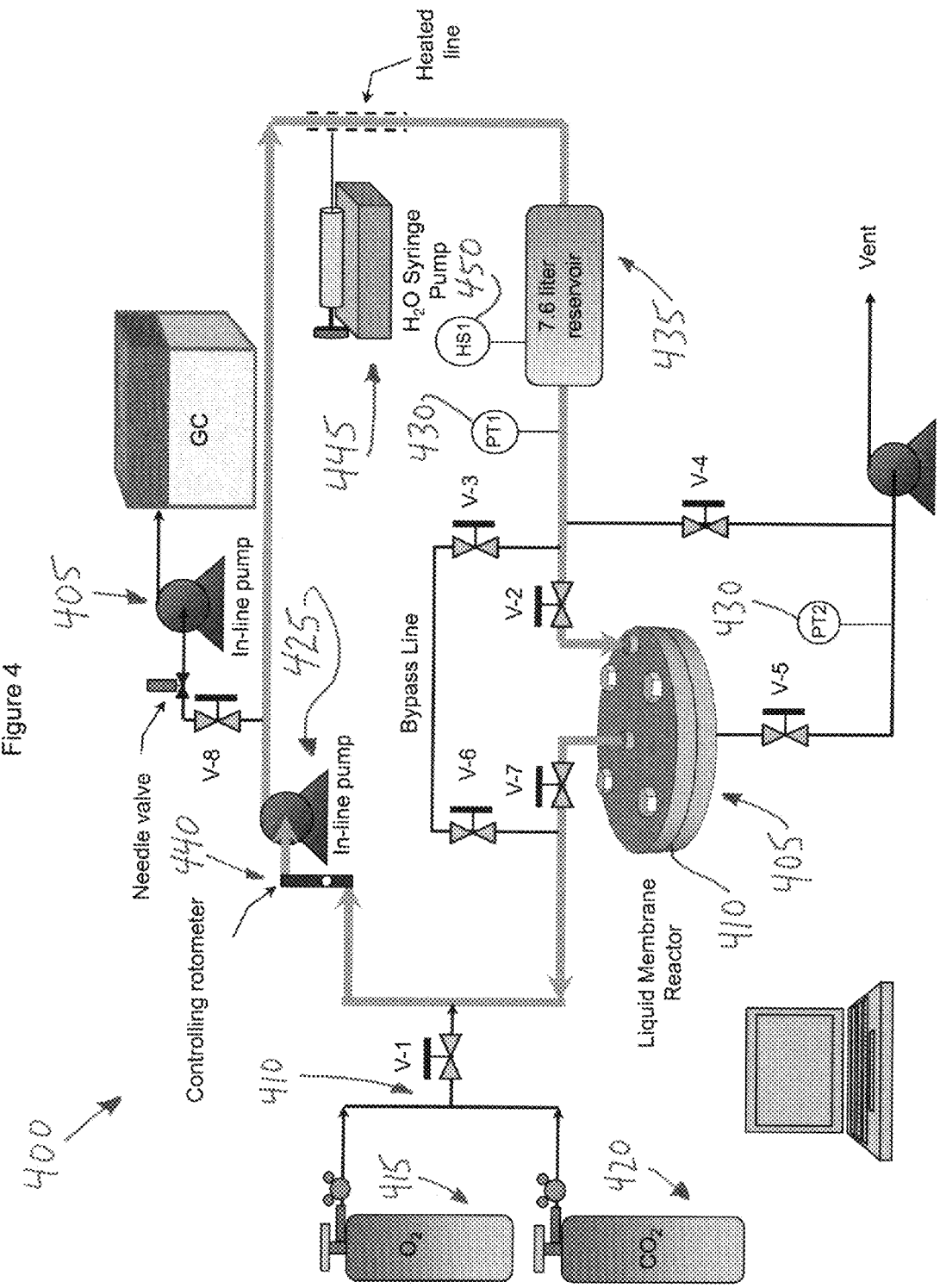
FIG. 4 illustrates an exemplary embodiment of a mixed gas test rig for SLM permeation testing.

Gas permeation tests were also conducted in a mixed gas test rig. With this rig, $CO_2$ permeation measurements could be made under more realistic conditions, in the presence of $O_2$ and $H_2O$, and exposure pressures down to 1 mm Hg were possible. A schematic of the membrane test rig 400 is shown in FIG. 4. The system includes the flow-through test cell 405 that holds the SLM 410, an oil-less scroll pump 405 to evacuate the loop, a gas manifold 410 to charge the loop with representative pressures of $O_2$ 415 and $CO_2$ 420, a diaphragm pump 425 to circulate the mixture, analytical instrumentation 430 to measure the changes in $CO_2$ and $H_2O$ concentrations, and an 8 liter reservoir 435. The mixture was circulated at a rate of about 17 slpm resulting in a circulation time of about 30 seconds. An in-line, vacuum rated rotameter 440 and valve controlled and monitor the flow in the loop. Water was introduced in two different ways. Initially a batch addition was made with an evaporator, which quickly charged the loop with humidity and then was isolated from the flow. The system was then modified and a Chemyx Fusion 100 syringe pump 445 was installed so that water could be added on a continual basis at a representative rate. A Vaisala-brand relative humidity sensor 450 was used to monitor the relative humidity (RH) in the mixed gas and the $CO_2$ concentration in the gas mixture was monitored with a gas chromatograph (GC). Finally, the system used LabVIEW-brand software and National Instruments-brand hardware for control and data acquisition.

To conduct gas permeation tests, the system was first evacuated to less than 50 mtorr and then the membrane was isolated by directing flow through the membrane bypass line. The loop and reservoir were then charged to 0.4 atm with a mixture consisting of low concentrations of $CO_2$ in $O_2$. In these tests the initial $CO_2$ concentration ranged from 0.75% to 2.5%, which correspond to a $CO_2$ partial pressure from 1.9 mm Hg up to 7.6 mm Hg. The circulation pump was started and at the same time the syringe pump was activated and water was injected at a rate of 8.0 μL/h to bring the humidity level up to the desired set point. Baseline GC measurements were obtained to verify that the expected $CO_2$ concentration was achieved in the loop. When the RH reached the desired starting point of about 25% RH, a second set GC analyses were obtained and then the process flow was switched from the membrane by-pass loop to the flow-through cell exposing the process flow to the SLM. Measurements of $CO_2$ concentration in the loop were made through the course of the experiment and used to calculate $CO_2$ permeance; the test was stopped when the $CO_2$ concentration had dropped to approximately half the original starting concentration. The $O_2$ permeance was calculated by monitoring total pressure and correcting for the loss of humidity and losses from the GC sampling.

Humidity addition was done in several steps. Initial tests were carried out in the mixed gas test rig without adding water. Then tests were conducted where the RH addition was done in a batch mode prior to exposing the flow to the membrane. The last step was to added water on a continual basis at a representative rate with a syringe pump. Results of each type of test are included below.

Membranes Tested

Figure 5:
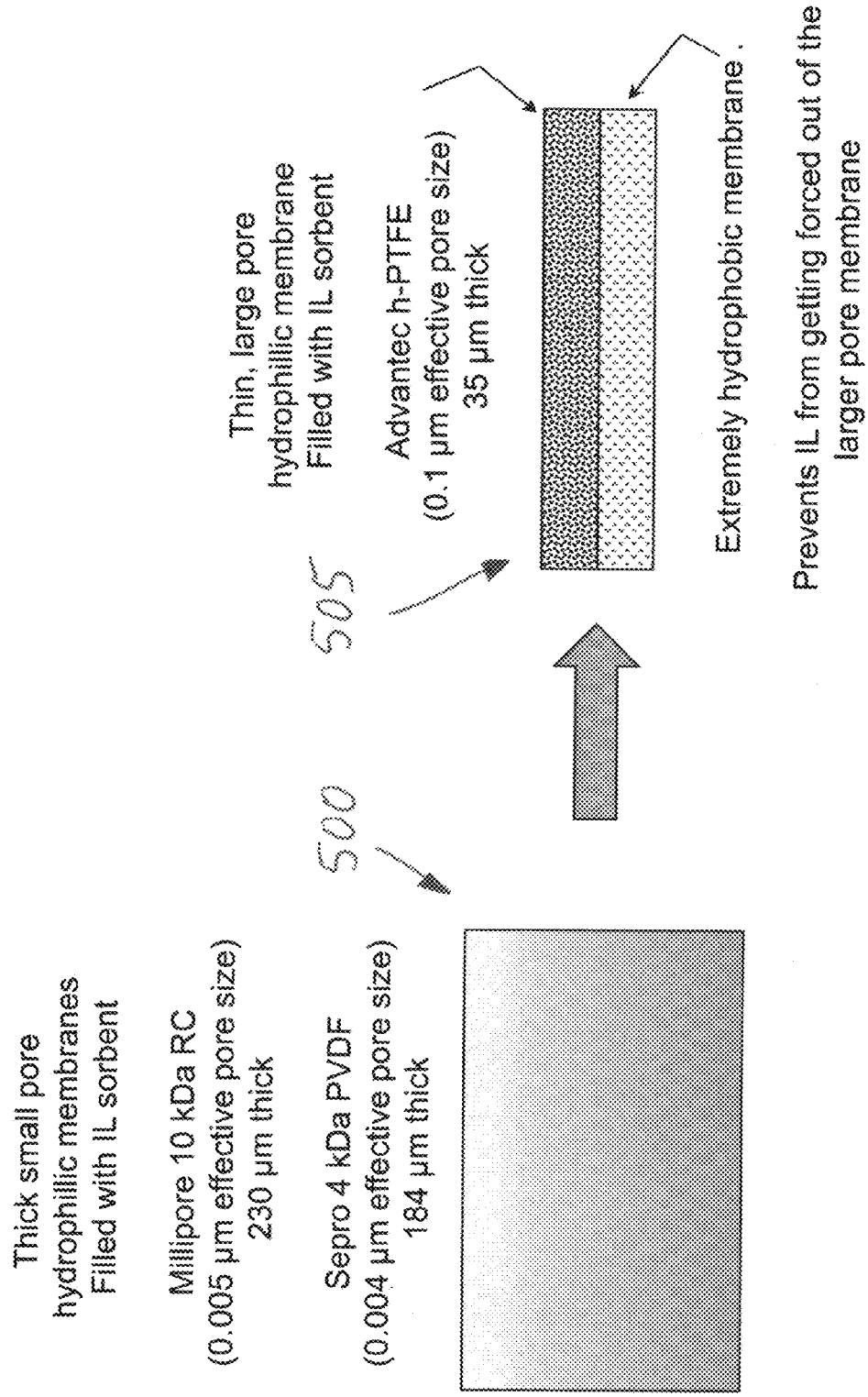
FIG. 5 illustrates exemplary embodiments of "layered membranes"

The two amine functionalized ionic liquids were tested on two different types of membranes. FIG. 5 illustrates a thick membrane 500 and a thin membrane 505. The thick membranes consisted of either Millipore regenerated cellulose (RC) or Sepro polyvinylidine fluoride (PVDF). The membranes were up to 230 μm thick and had a molecular weight cutoffs as low as 4,000 Daltons (4 kDa), corresponding to a minimum pore size of 0.004 μm. The thin membrane consisted of two layers of Advantec PTFE that were only 35 μm and had pore sizes of 0.1 μm. The layer on the high pressure side was treated to make it hydrophilic (h-PTFE) while the bottom layer was hydrophobic (PTFE). The ionic liquid was contained in the h-PTFE layer and the presence of the hydrophobic layer on the low pressure side prevented the ionic liquid sorbent from being forced out of the pores of the h-PTFE membrane.

Spectroscopic Characterization of IL

Figure 6:
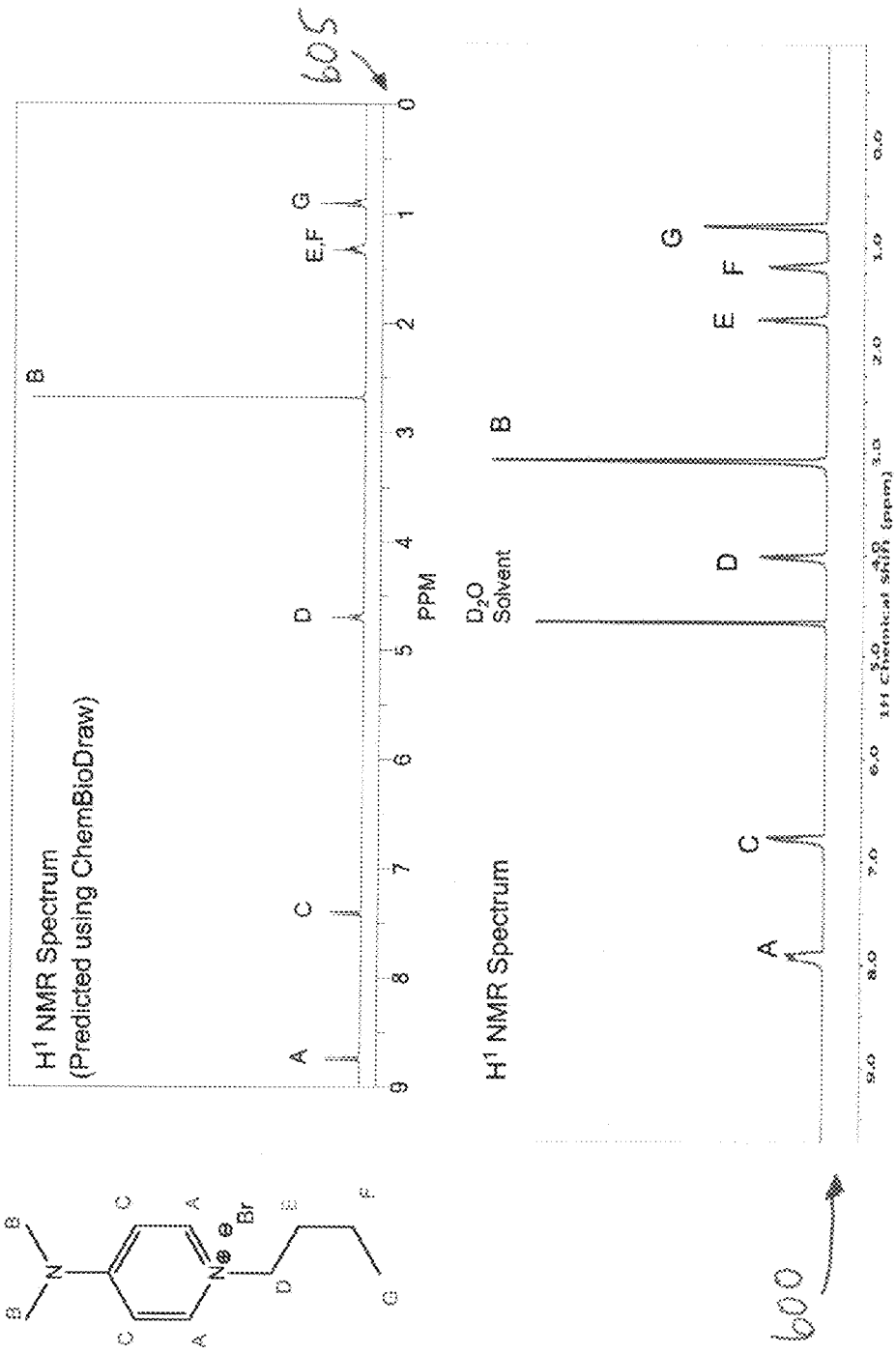
FIG. 6 illustrates NMR predicted and measured spectra of the 1-butyl-4-(dimethylamino)pyridinium compound.
Figure 7:
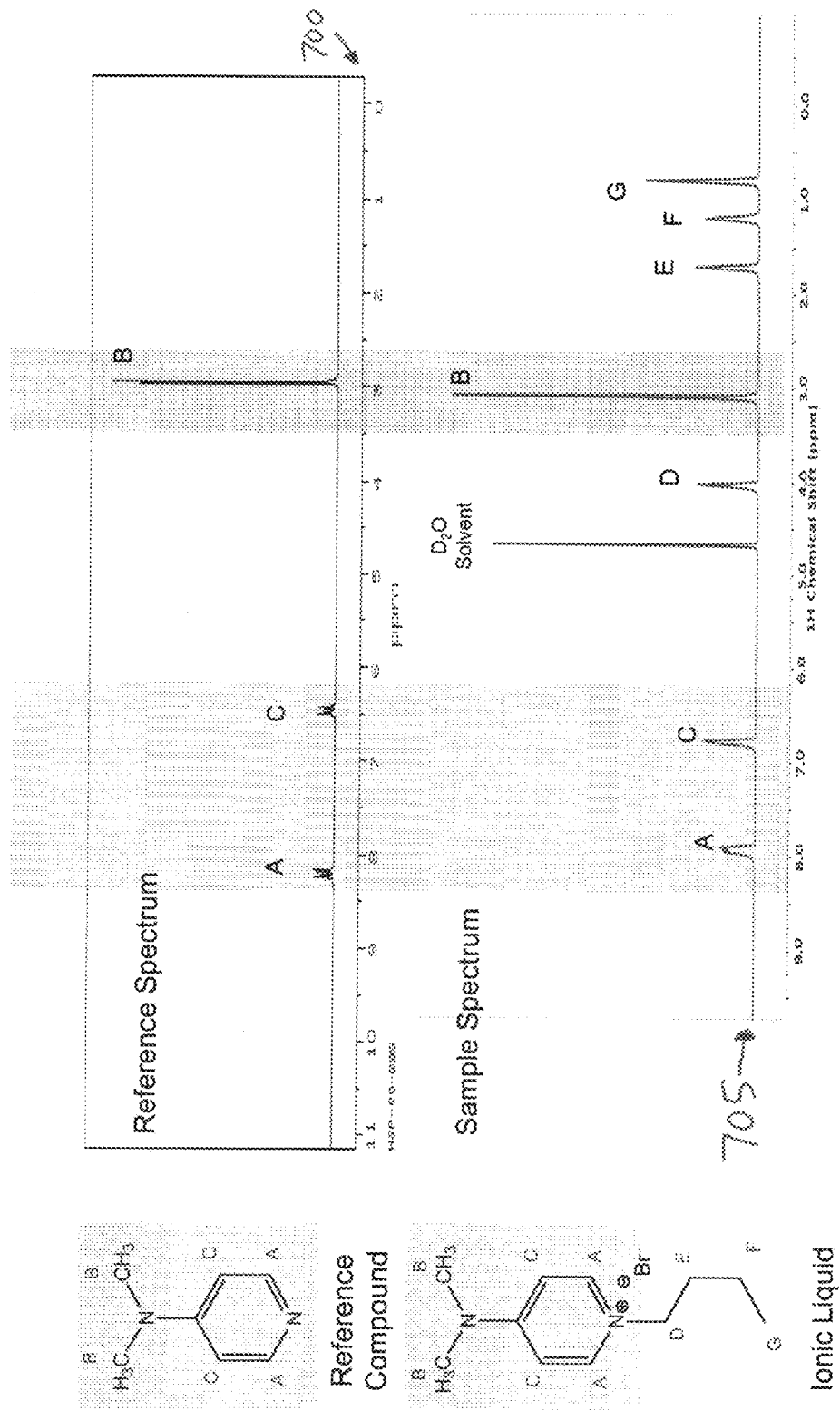
FIG. 7 illustrates NMR reference spectrum of 4-(dimethylamino)pyridine (top) and the NMR spectrum obtained for 1-butyl-4-(dimethylamino) pyridinium compound prepared in our laboratory (bottom)
Figure 8:
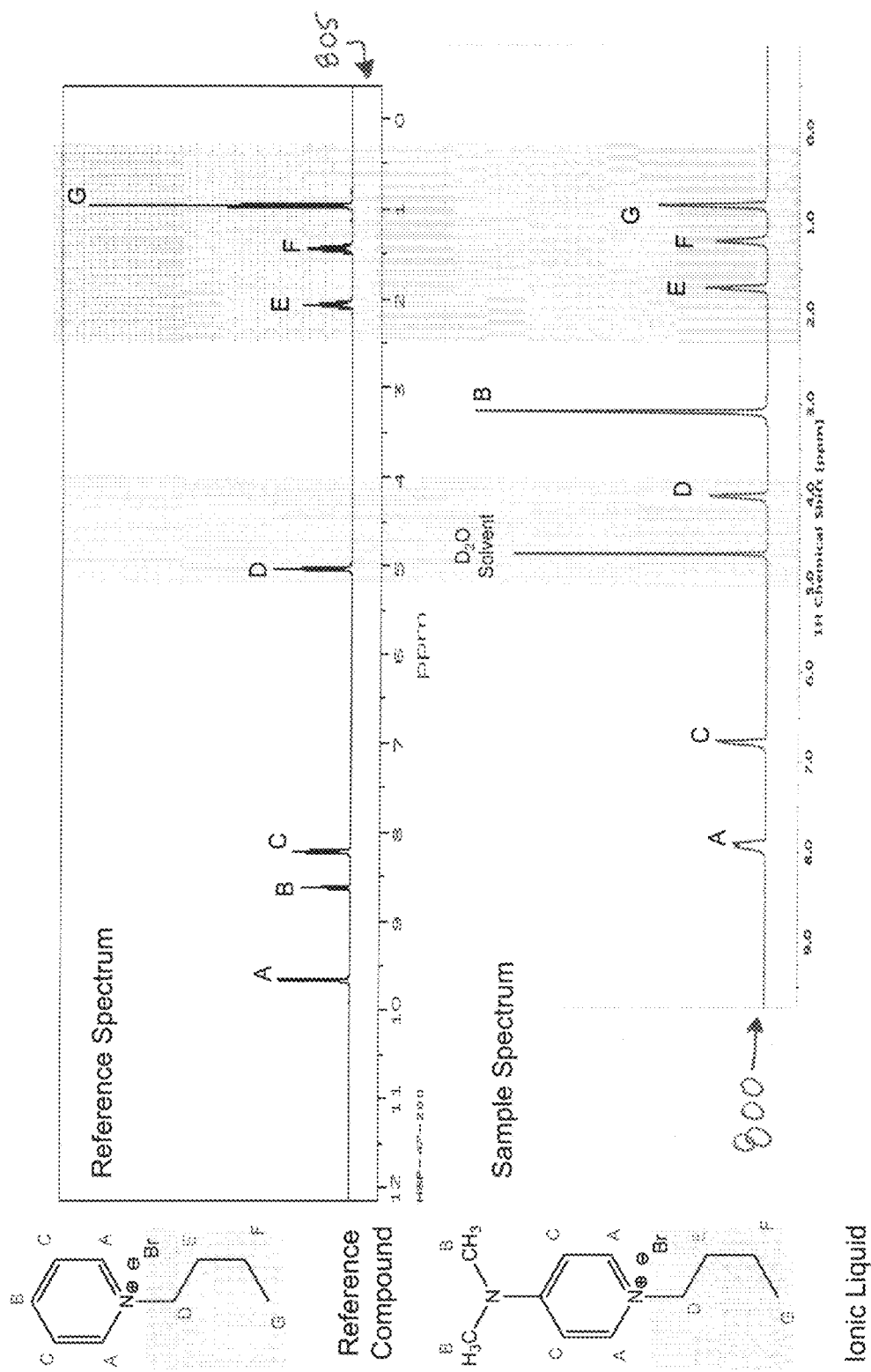
FIG. 8 illustrates NMR spectrum of the 1-butyl-4-(dimethylamino)pyridinium compound prepared by Reaction Systems and a reference spectrum of 1-butylpyridine.
Figure 9:
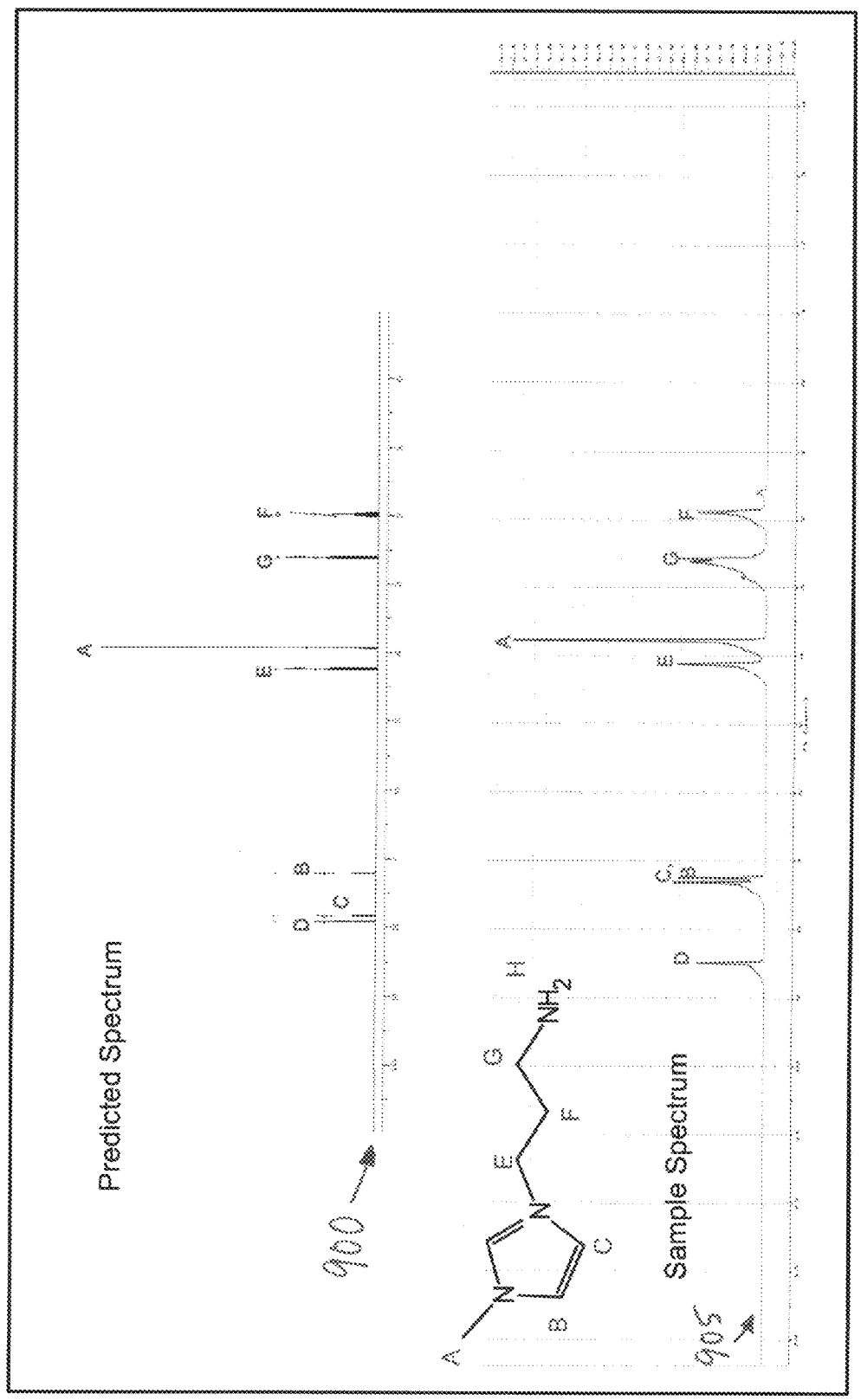
FIG. 9 illustrates predicted and measured NMR spectra of the AP-Mim.

The NMR results obtained for B-DMAPyr are shown in FIG. 6, FIG. 7, and FIG. 8 while the results obtained for the primary amine containing compound AP-Mim are shown in FIG. 9. In FIG. 6, the NMR spectrum obtained on B-DMAPyr 600 is presented in the bottom of the figure, while the predicted spectrum 605, from a commercial software package, ChemBioDraw, is shown at the top of the figure. Overall, there is a good match between the predicted and actual results. All the peaks predicted from the software are present in the actual spectrum although there are some shifts in the actual location. Perhaps most important are the presence of peaks that correspond to the point in the molecule where the attachment of the butyl group to the pyridinium compound occurred. In this case the presence of protons on the carbon atoms labeled D, E, F, and G would be the most relevant. Although there is some difference in the locations of the peaks, their relative positions are consistent and the shift can be due to errors in the predictions since these are new compounds.

To better clarify the peak assignments, NMR spectra were compared from parts of the ionic liquid molecule to those from existing molecules. In FIG. 7 a reference spectrum 700 for 4-dimethylaminopypridine (top) is compared to that obtained for the prepared compound 705 (bottom). As shown the peak locations are similar in both spectra. For example, the peak that corresponds to the hydrogen atoms on the amino groups of dimethylaminopyridine (labeled B on the molecule) is very similar in location and intensity to the peak obtained in our spectrum. In addition peaks corresponding to the hydrogen atoms on the ring (A and C) are also similar in location to those obtained in our spectrum. This shows that the dimethylaminopyridine structure is contained in the ionic liquid. This is not unexpected since 4-(dimethylamino)pyridine was used in the synthesis.

However, FIG. 8 provides good evidence that the desired ionic liquid has indeed been prepared. The figure shows that the portion of the NMR spectrum obtained on our sample 800 that corresponds to the butyl group is very similar to the reference spectrum of 1-butylpyridine. In this case, the presence and location of the peaks corresponding to the hydrogen atoms on the carbons of the butyl chain, D, E, F, and G compare well to those in the reference spectrum 805, showing clearly that the butyl group was successfully attached to the 4-dimethylaminopyridine precursor. Since the attachment of the butyl group was the primary step in the synthesis of this amine functionalized ionic liquid, these results show that the synthesis was successful.

FIG. 9 shows the predicted (top) 900 and actual (bottom) 905 spectra for AP-Mim. In this case, there is a good match between the predicted spectra and those observed. Of particular importance are the peaks corresponding to the protons labeled E, F, and G since these are part of the butyl group that was attached to the imidazolium ring during the synthesis. The figure shows that there is a good match between the peaks predicted by the ChemBiodraw software and those obtained in the NMR analysis. Overall the NMR results obtained provide good evidence that the desired compounds were synthesized.

Figure 10:
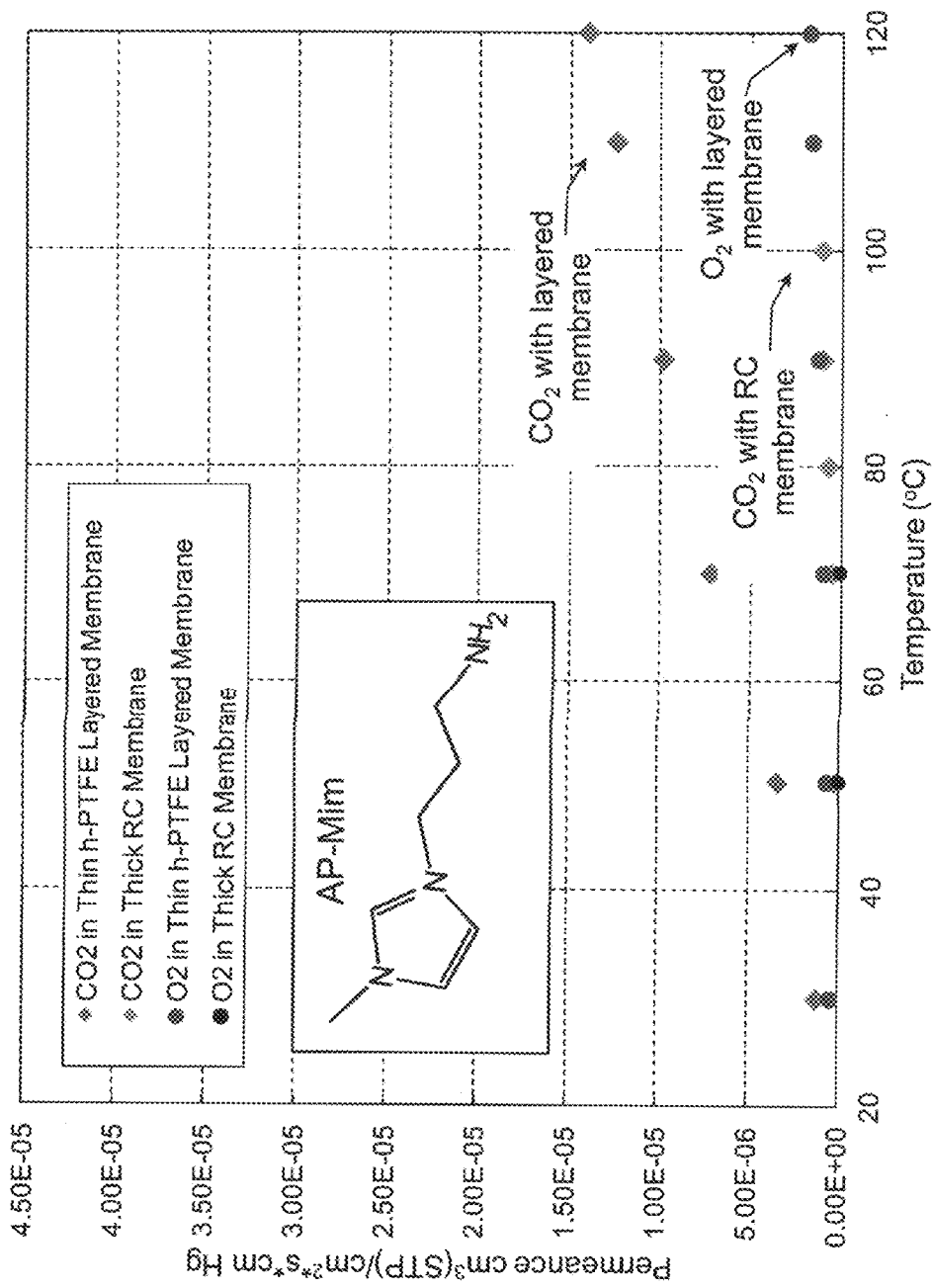
FIG. 10 illustrates permeance results with the thin layered membrane.

Results of Membrane Permeation Tests in the Thin, Layered Membrane Tests at $CO_2$ Pressure of 0.2 atm FIG. 10 shows the effect of using the thin, layered membrane in the SLM with the AP-Mim sorbent. The figure includes $CO_2$ permeation data obtained on the thin, layered membrane along with data obtained on the thicker, regenerated cellulose (RC) membrane. The latter membrane was 230 μm thick and has a molecular weight cutoff of 10,000 Daltons (10 kDa), corresponding to an effective pore size of 0.005 μm. In both cases, tests were carried out at membrane temperatures from 30° C. to 120° C. and at $CO_2$ exposure pressures of 0.2 atn. As shown, switching to the thinner membrane resulted in significant increases in $CO_2$ permeance. For example at 70° C., the permeance in the RC membrane was 5.08E-7 scc/($cm^2$-s-cm Hg). However, in the thinner, layered membrane the permeance increased to 7.22E-6 scc/($cm^2$-s-cm Hg), which is over a factor of 10 increase. At the highest temperature of 120° C., the $CO_2$ permeance was 1.4E-5 scc/($cm^2$-s-cm Hg), which is high enough to meet the permeance requirement. However, the figure also shows that at 70° C., the $O_2$ permeance was 9.3E-7 scc/($cm^2$-s-cm Hg); therefore the $CO_2/O_2$ selectivity at this temperature was less than 10, which does not meet the selectivity requirement.

Figure 11:
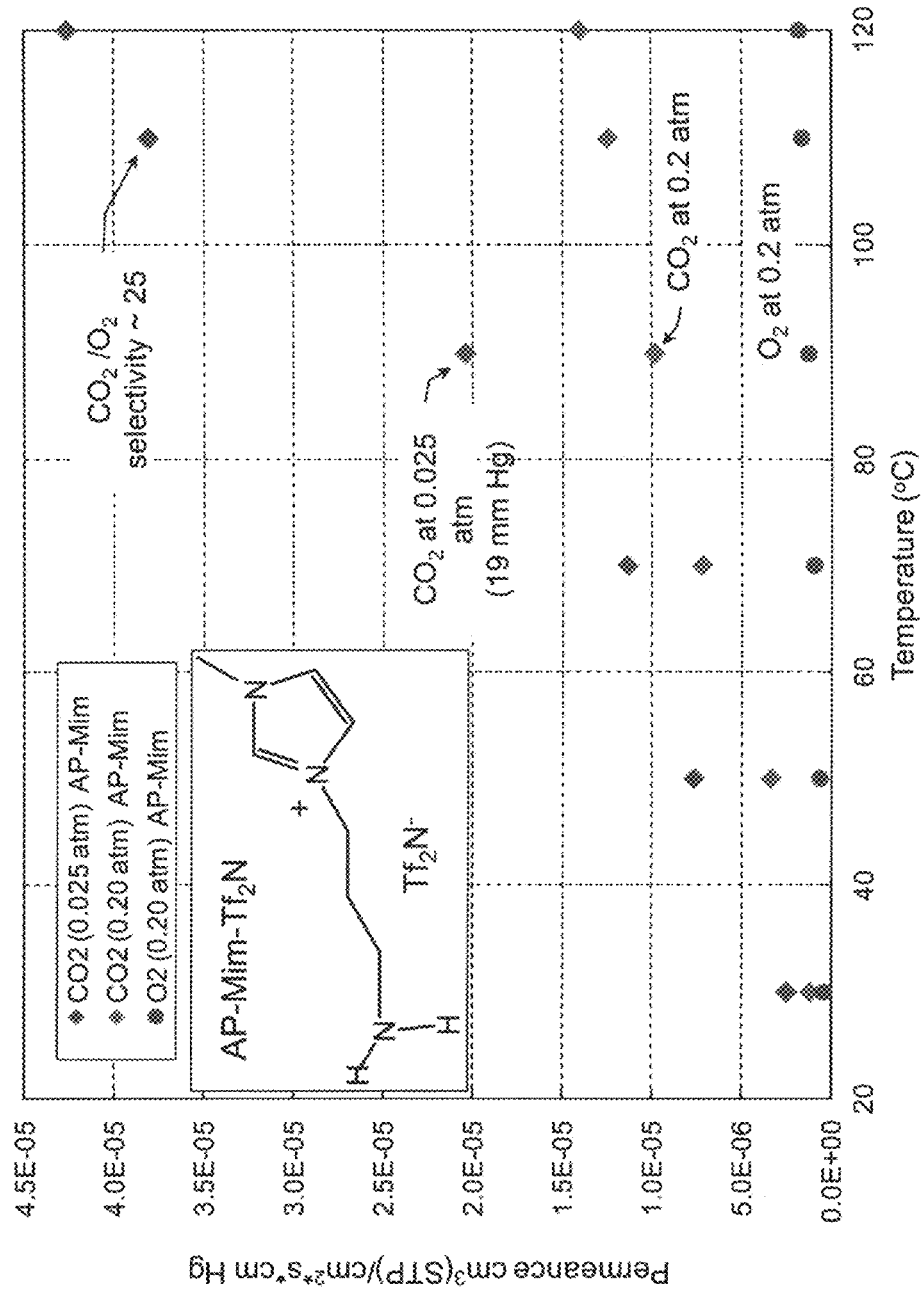
FIG. 11 illustrates permeance results at low CO2 pressures.

Although these tests produced accurate measures of $CO_2$ permeance through the membrane, the $CO_2$ exposure pressures used, 0.2 atm, were much higher than would be permitted in a space suit. Therefore in order to conduct tests under more realistic conditions, the exposure pressure was reduced by a factor of 10 and conducted tests at pressure of 0.025 atm or 19 mm Hg. The results of these tests are shown in FIG. 11. The results obtained at the higher exposure pressures are included in the figure for comparison. Reducing the $CO_2$ exposure pressure resulted in significant increases in $CO_2$ permeance and because the $O_2$ partial pressure is not being changed, the effect translates directly into significant increases in $CO_2/O_2$ selectivity. For example at 90° C., reducing the $CO_2$ pressure from 0.2 atm to 0.025 atm increased the $CO_2$ permeance from 9.8E-6 to 2.0E-5 scc/($cm^2$-s-cm Hg), or by about a factor of 20. At 110° C. the $CO_2$ permeance increased from 1.3E-6 to 3.7E-5 or by a factor of 28. Moreover, at this condition the $CO_2/O_2$ selectivity is 25, which represents a significant increase over the selectivities that were obtained at the higher $CO_2$ exposure pressure of 0.2 atm.

Tests at $CO_2$ Pressures of 0.025 atm

The increase in $CO_2$ permeance observed when the $CO_2$ exposure pressure was decreased from 0.2 atm to 0.025 atm is referred to as facilitated transport and it has been reported previously. Although 0.025 atm (19 mm Hg) is significantly lower than the pressures used previously, it still is higher than would be permitted in a space suit. Therefore, there was a need to characterize the performance of the SLM under more representative $CO_2$ pressures, less than 2 mm Hg. In addition, the $CO_2$ permeance in a mixed gas including water needed to be determined. Therefore, switch was made to the mixed gas test rig for additional tests.

Humidity addition was done is several steps. Initial tests were carried out in the mixed gas test rig without adding water. Then tests were conducted where the RH addition was done in a batch mode prior to exposing the flow to the membrane. The last step was to added water on a continual basis at a representative rate with a syringe pump. Results of each type of test are included below.

Mixed Gas Test Results without Humidity Addition

Figure 12:
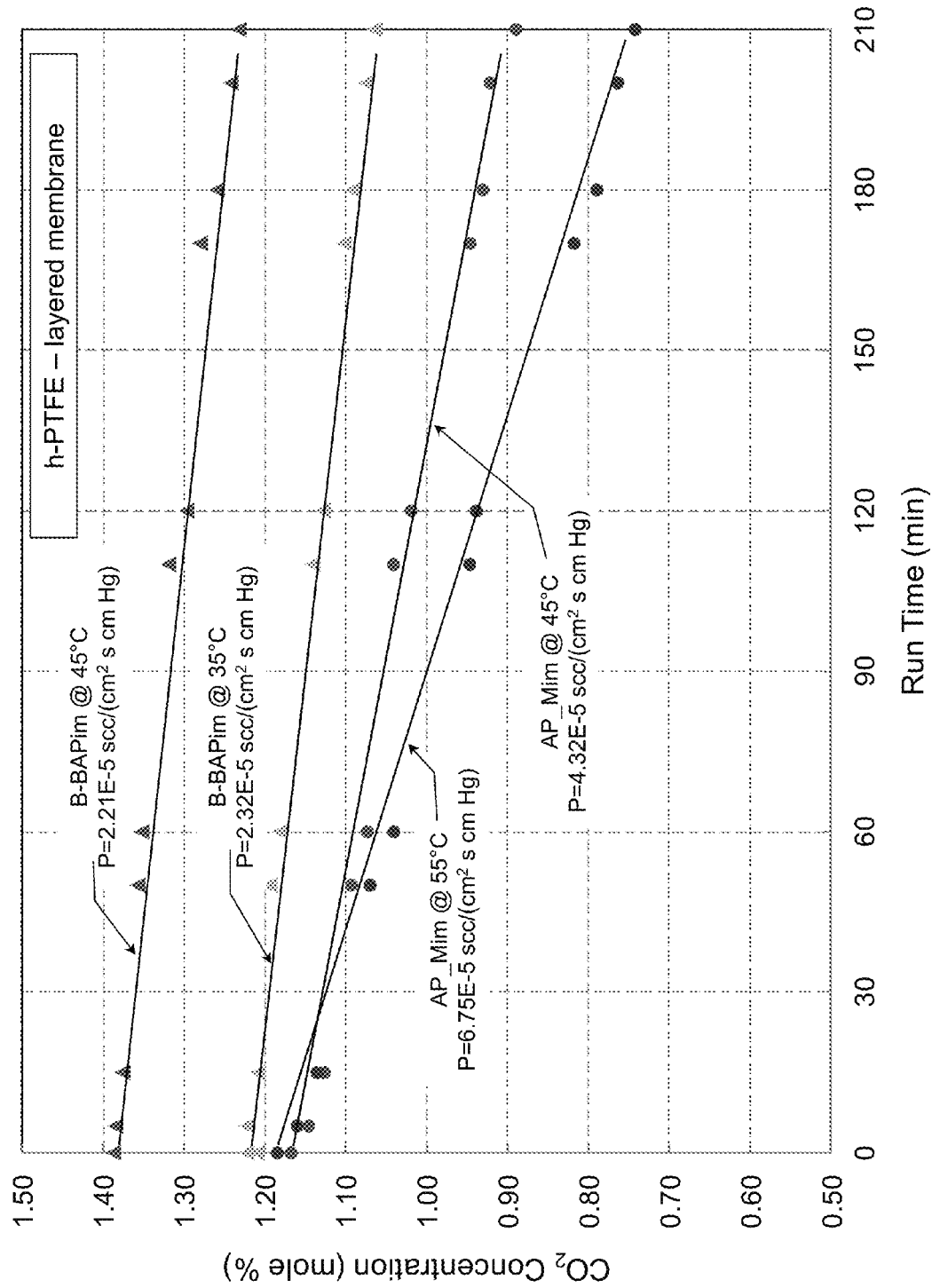
FIG. 12 illustrates measured $CO_2$ concentrations in the circulating loop with two different ionic liquid solutions at membrane temperatures ranging from 50 to 90° C.

The results of four mixed gas tests, two with AP-Mim and two with B-BAPim are shown in FIG. 12. The figure shows the $CO_2$ concentration measured in the flow loop with the GC as a function of membrane exposure time. In all cases the $CO_2$ concentrations decreased at a relatively constant rate, so that all points in each test fall close to a straight line. For the tests with the AP-Mim, the starting concentrations were approximately 1.18 mole % which corresponds to a $CO_2$ partial pressure of approximately 3.5 mm Hg. The figure shows that the rate of decrease in $CO_2$ concentration measured for the AP-Mim at 55° C. was greater than that obtained at 45° C. The slopes of the lines to calculate average permeance values for each test and obtained a value of 6.75E-5 scc/($cm^2$ s cm Hg) for the tests at 55° C. and 4.32E-5 scc/($cm^2$ s cm Hg) for the test carried out at 45° C.

Comparing these permeance values to those reported in the previous figure shows that higher values were obtained at the $CO_2$ pressures. For example, the maximum value obtained in these tests, 6.75E-5 scc/($cm^2$ s cm Hg) is almost 50% higher than the maximum value reported in FIG. 11. Obtaining higher permeance values at reduced $CO_2$ pressures is a characteristic of facilitated transport where there is a chemical reaction between the sorbent and $CO_2$. This characteristic has been discussed previously and is the result of the increased efficiency of the reaction between the sorbent and $CO_2$ as the concentration of $CO_2$ is reduced. (Hanioka S., Maruyama T., Sotani, T., Teramoto, M., Matsuyama, H., Nakashima, K., Hanaki, M., Kubota, F., and Goto, M. "CO2 Separation Facilitated by Task Specific Ionic Liquids Using a Supported Liquid Membrane," Journal of Membrane Science, 314, pp. 1-4, 2008.)

The results obtained for the secondary amine, B-BAPim $TF_2N$ at 35° C. and 45° C. are also contained in this figure. Initial inspection shows two significant differences from the data obtained with the AP-Mim. First in both cases, the slopes are noticeably lower than both of those obtained for the primary amine. The permeance values obtained for this compound at 35° C. and 45° C. were 2.32E-5 scc/($cm^2$ s cm Hg) and 2.21E-5 scc/($cm^2$ s cm Hg) respectively and these values are about a factor of two lower than the values obtained with the primary amine. In addition, the results with the secondary amine showed that increasing the temperature decreased the permeance value by a small amount. On the other hand, it was seen that increasing the temperature by 10° C. with the primary amine resulted in about a 50% increase in permeance.

Figure 13:
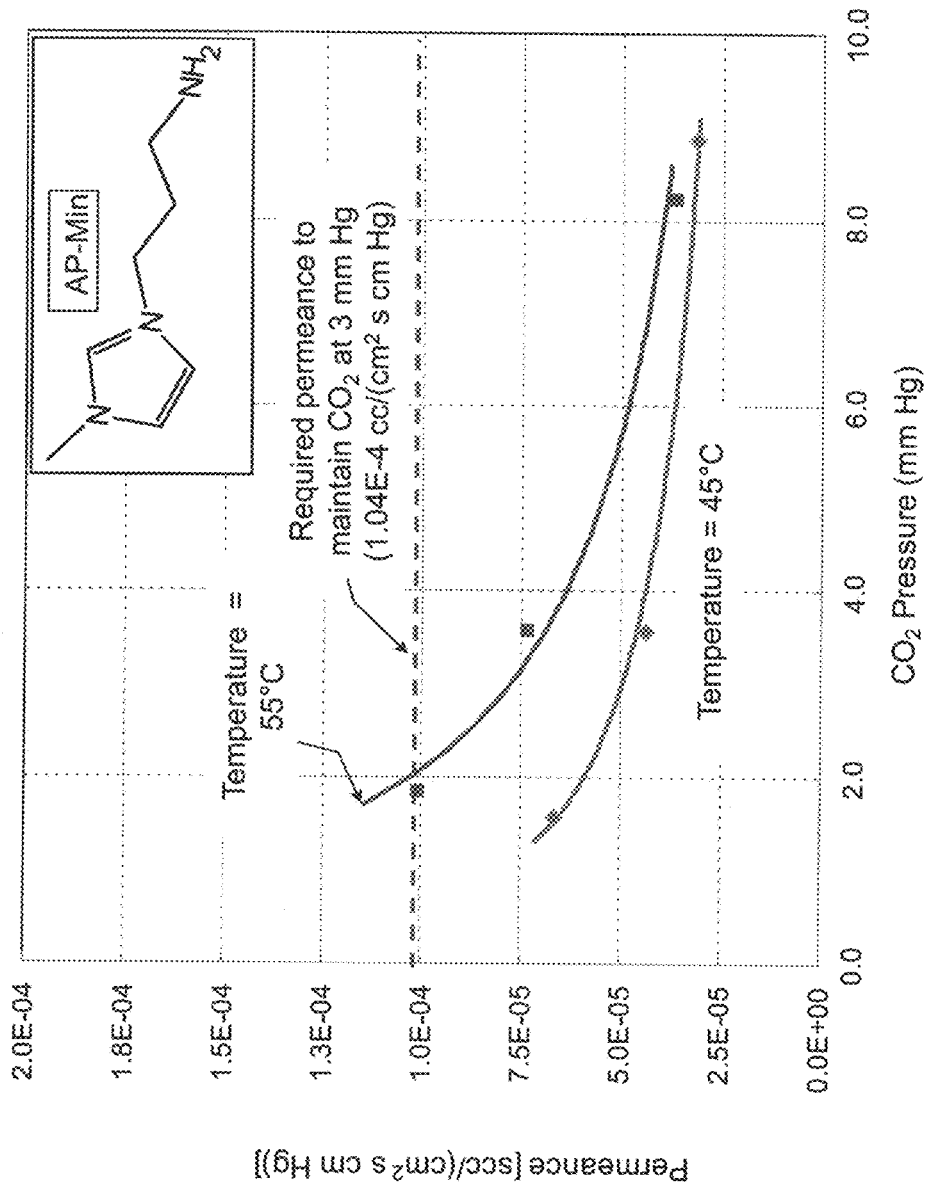
FIG. 13 illustrates permeance values obtained with the AP-Mim at 45° C. and 55° C. as a function of $CO_2$ pressure.

Additional tests were also carried out with starting $CO_2$ concentrations of 2.5 and 0.5 mole % which correspond to partial pressures of approximately 8 and 2 mm Hg respectively. The permeance values obtained in these tests are shown in FIG. 13. The figure includes best fit lines of permeance as a function of concentration at both temperatures along with the permeance needed to support the average production rate of an astronaut while maintaining a maximum concentration of 3 mm Hg. The figure shows that at both temperatures, the permeance values increased as the initial concentration was reduced. At 45° C., a permeance of 3.14E-5 scc/($cm^2$ s cm Hg) was obtained at a $CO_2$ partial pressure of 8.9 mm Hg, while at a lower pressure of 1.6 mm a permeance of 6.69E-5 scc/($cm^2$ s cm Hg) was obtained. This represents over a factor of two increase in permeance obtained by going to the lower $CO_2$ exposure pressure. At 55° C., the difference was even greater. At 8.83 mm Hg, a permeance of 3.89E-5 scc/($cm^2$ s cm Hg) was obtained, while at 1.9 mm Hg, the permeance increased to 1.04E-4 scc/($cm^2$ s cm Hg).

FIG. 13 includes an estimate of the permeance that would be needed to control $CO_2$ in a suit assuming an average $CO_2$ generation rate of 93 g/h and that the module volume limit is 0.25 $ft^3$. With a hollow fiber configuration, the module could contain a surface area of 50 $m^2$ which then sets the flux at 3.12E-5 scc/($cm^2$ s) and if the $CO_2$ concentration is limited to 3 mm Hg, then the required permeance is 1.04E-4 scc/($cm^2$ s cm Hg). Therefore this shows that at 90° C. the flux needs to be increased by about 25% to reach the required permeance at a $CO_2$ concentration of 3 mm Hg.

Mixed Gas Test Results with Batch Water Addition

Although the results in the mixed gas tests with the AP-Mim showed that the permeance values were approaching those needed to control $CO_2$, the $O_2$ permeance values were still too high resulting in a $CO_2/O_2$ selectivity of 89. Although this is a much higher value than can be obtained by conventional membranes, it is well below the 1300 threshold that was identified earlier. Therefore a different anion was switched to which has been suggested to be more resistant to $O_2$ permeation. In addition, water addition was switched to a continual mode using a syringe pump.

Figure 14:
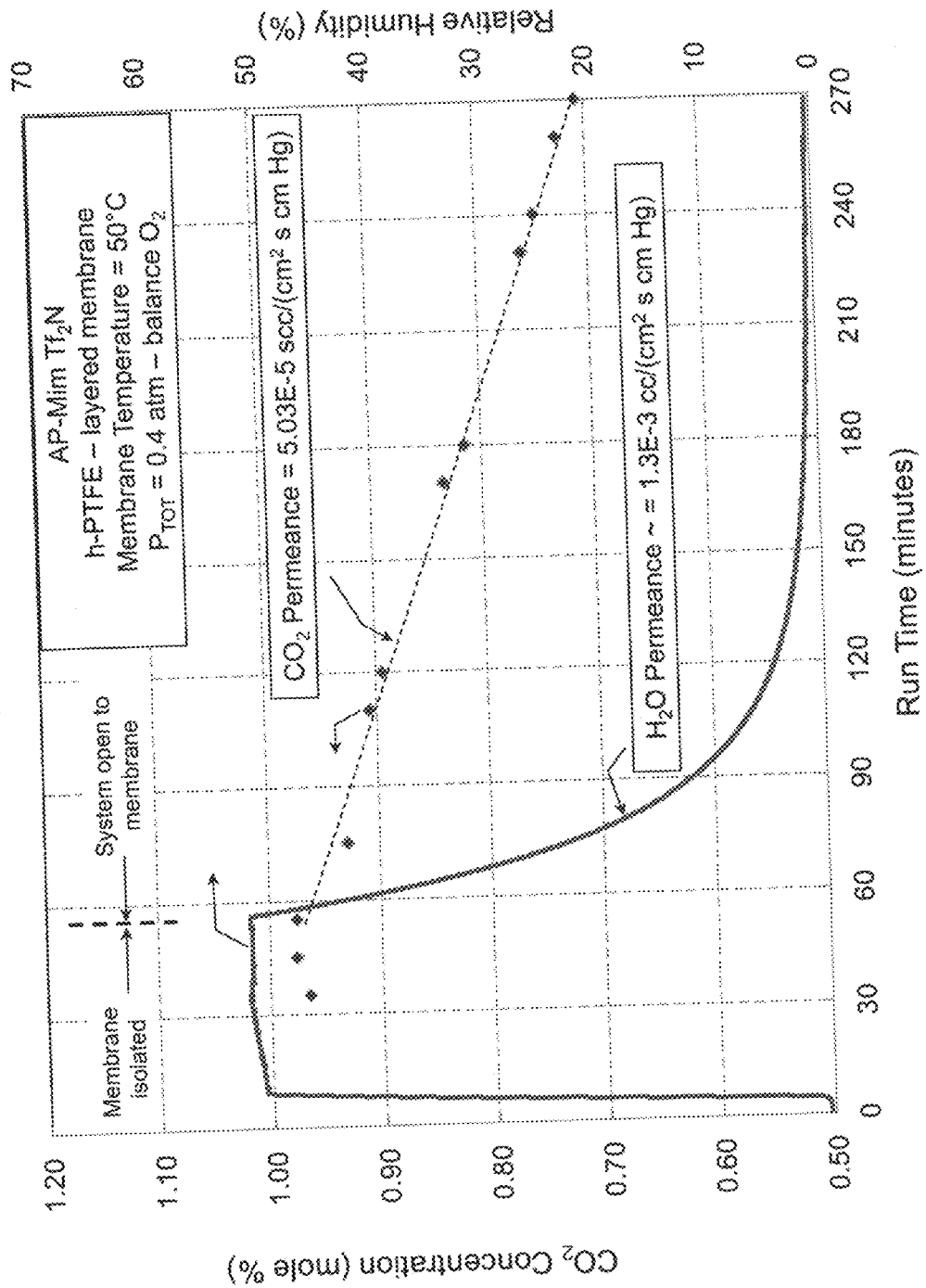
FIG. 14 illustrates $CO_2$ and relative humidity as a function of run time exposed to an SLM with the AP-Mim $Tf_2N$.

The results of the initial test carried out in this series is shown in FIG. 14. The figure shows that before the loop flow is open to the membrane, the relative humidity is stable at approximately 52% and the $CO_2$ values are also relatively constant at 0.98 mole % which corresponds to approximately 4 mm Hg. At a run time of 58 minutes, when the loop was open to the membrane, the figure shows that the humidity dropped rapidly reaching a value of about 10% at a time of 92 minutes or after only 30 minutes exposure to the membrane. As shown the humidity continued to drop and finally reached a value of less than 1% at the end of the test.

The data used in the test to calculate an average $H_2O$ permeance and obtained a value of 1.3E-3 scc/($cm^2$ s cm Hg). This value is a about a factor of 50 greater than the $CO_2$ permeance and indicates that the membrane could control the humidity levels in a space suit to very low levels, probably less than 5%.

Figure 15:
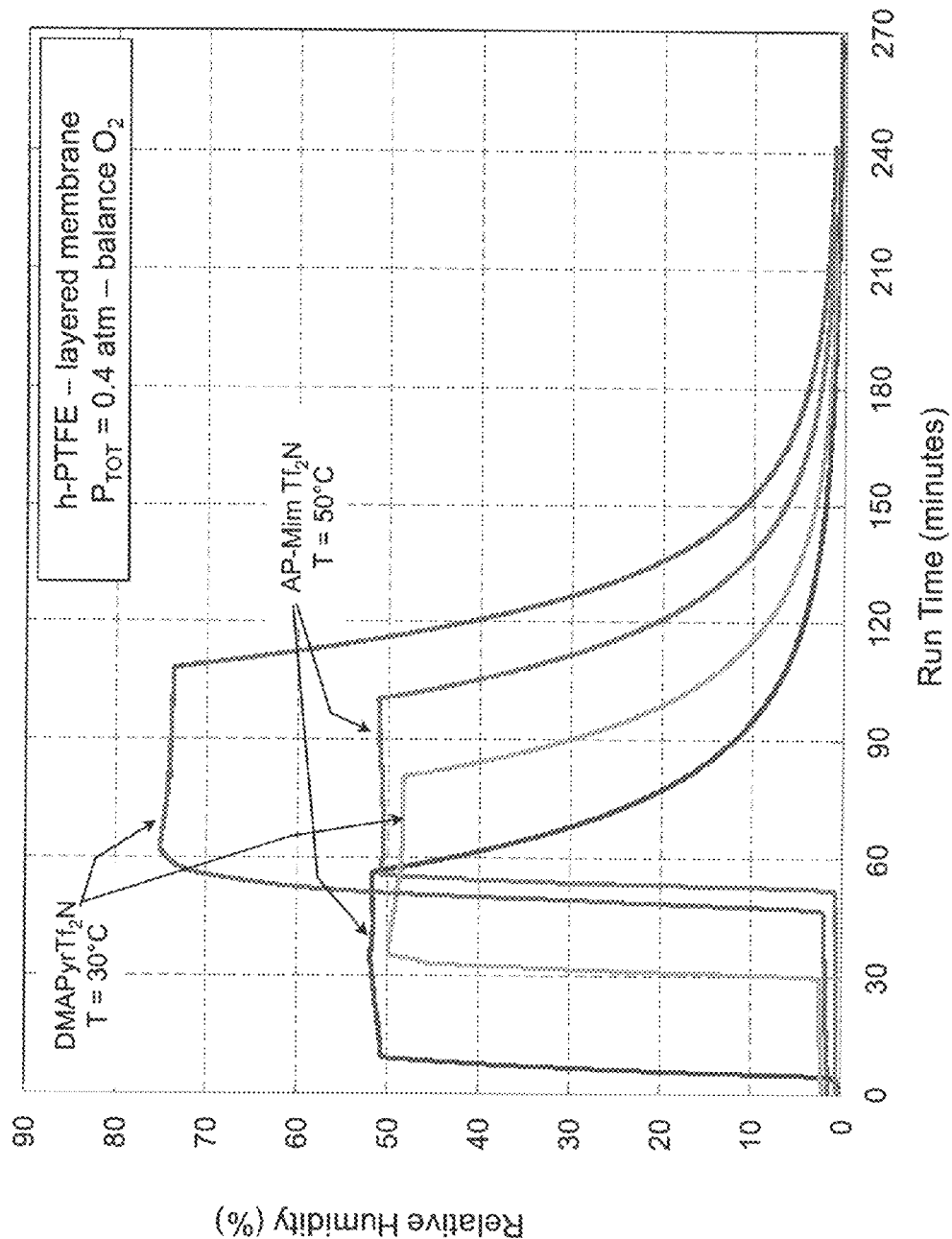
FIG. 15 illustrates relative humidity as a function of time for two tests with a primary amine, AP-Mim, and two tests with a tertiary amine, DMAPyr.

Three additional tests were carried out using this method. One was conducted with the same ionic liquid, AP-Mim at the same temperature and two tests were carried out with a tertiary amine, D-MAPyr at 30° C. The results of all of these tests are shown in FIG. 15. As shown, in three of the tests, the initial humidity was set to about 50%. However in the fourth test, the initial humidity level was adjusted to 75%. Regardless of the initial humidity, all tests show that once the circulating loop was open to the membrane, the humidity levels dropped rapidly, and produced H2O permeance values that were are approximately 1.0E-3, significantly greater than those obtained for $CO_2$.

Tests with AP-Mim BF4 Constant Rate of Water Addition

Literature indicated that the $BF_4$ anion is more resistant to $O_2$ permeation. Therefore syntheses were carried out using this form of the AP-Mim. In this test, a syringe pump was also used to inject water vapor into the loop at a constant rate.

Figure 16:
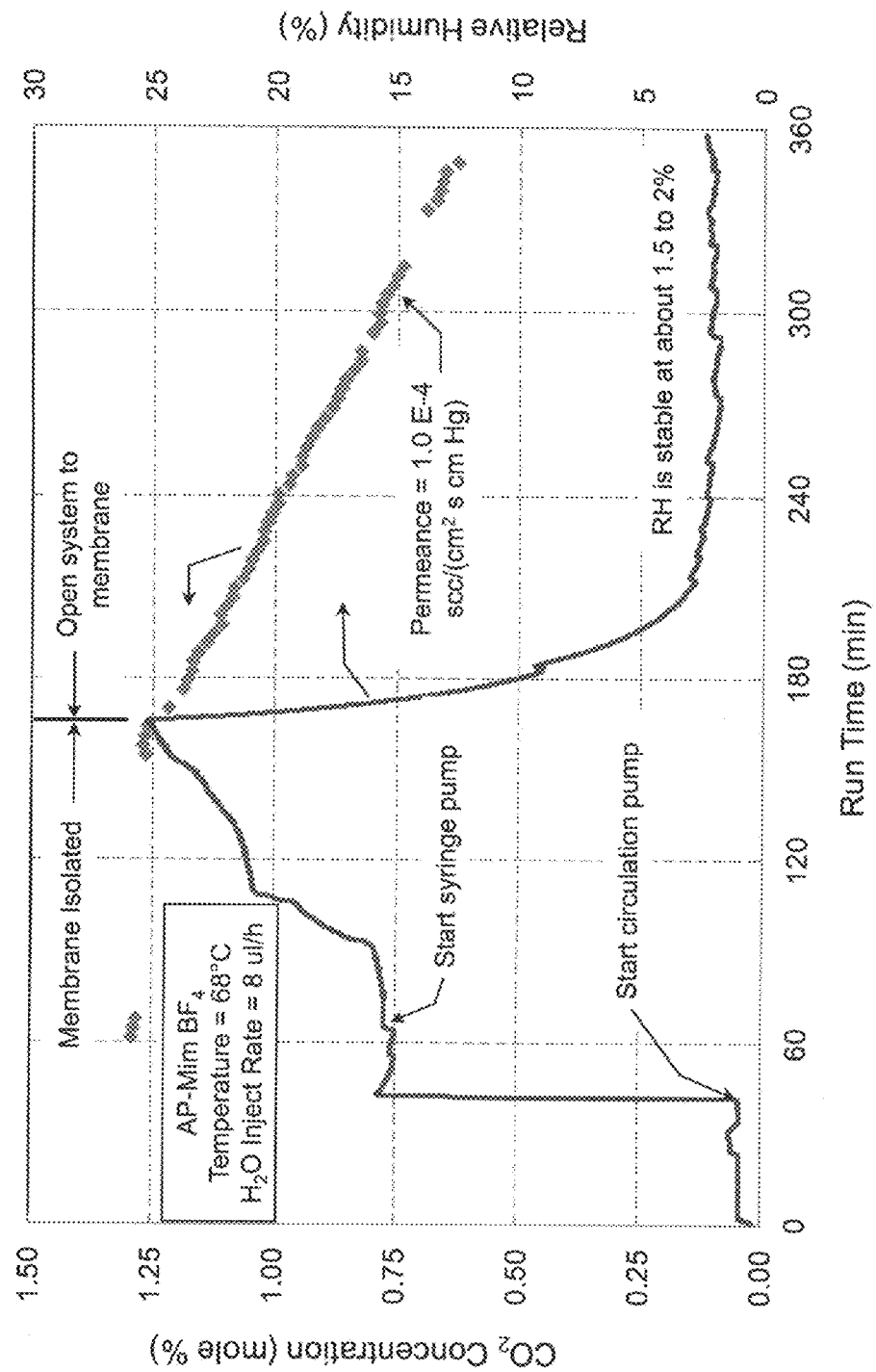
FIG. 16 illustrates $CO_2$ concentration and moisture as a function of time with the AP-Mim-$BF_4$ at 68° C.
Figure 17:
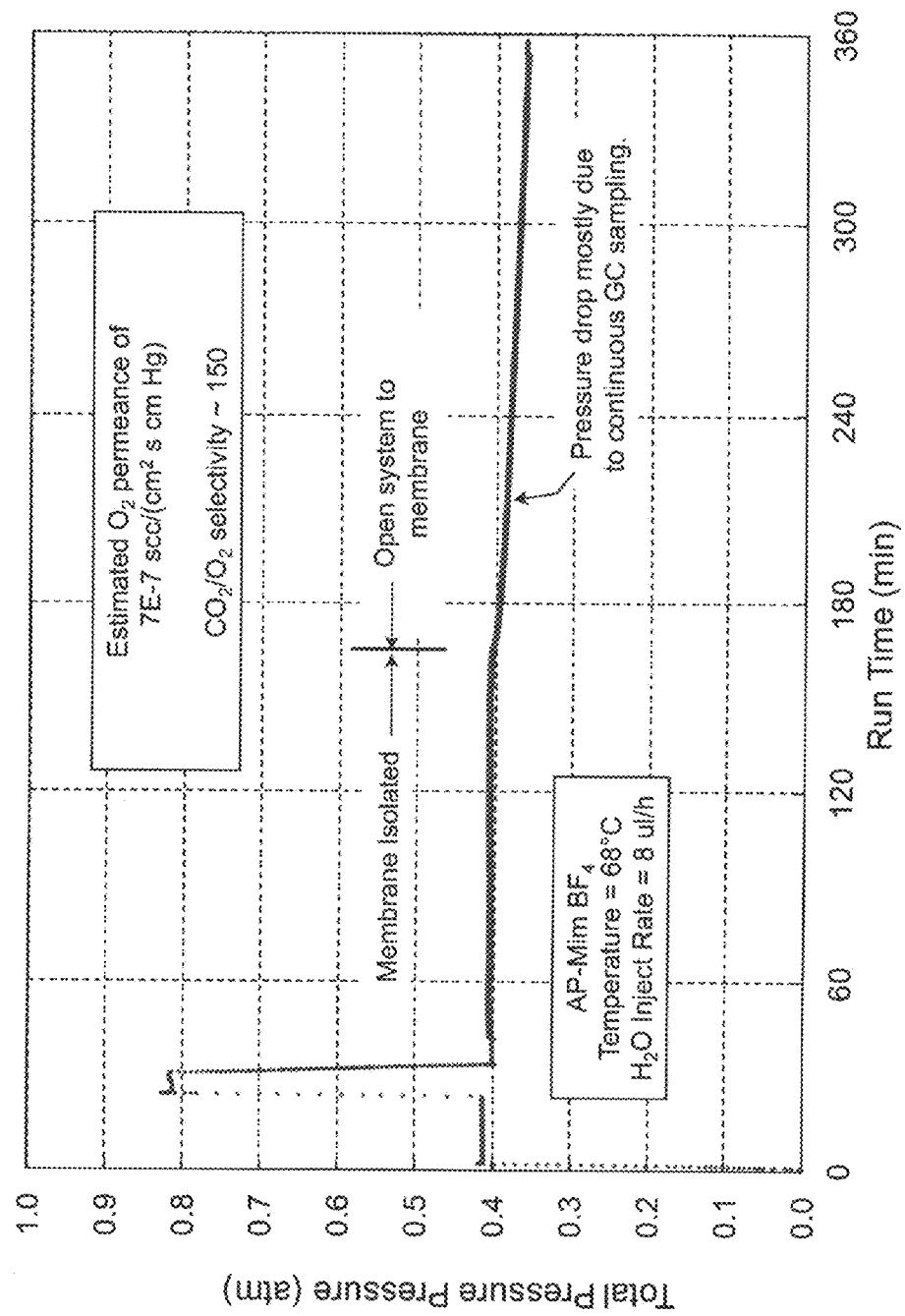
FIG. 17 illustrates total pressure as a function of time with the AP-Mim-$BF_4$ at 68° C.

The results of an initial test with this compound are shown in FIG. 16 and FIG. 17. FIG. 16 shows the $CO_2$ concentration, plotted on the left axis, and the relative humidity profile, on the right axis, as a function of time, both before and after the circulating loop was exposed to the membrane. Between time zero and 41 minutes, the large reservoir and loop were charged with $CO_2$ and $O_2$, using the procedure described above, such that the membrane containing the ionic liquid sorbent was not yet exposed to the gas. At a time of 41 minutes, the circulation pump was activated which brought the relative humidity level up to 15%. After maintaining these conditions for 15 minutes, the syringe pump was activated and a $CO_2$ measurement was measured with the gas chromatograph. As shown, three similar values were obtained that averaged 1.29 mole %. FIG. 17 shows that the total pressure of the system is 0.41 atm and therefore a concentration of 1.29% is equivalent to a partial pressure of 4 mm Hg. At 65 minutes, the syringe pump was activated which caused the relative humidity to climb to 25% as expected and at 160 minutes another set of GC analyses were obtained that show the $CO_2$ concentration was remaining relatively constant. Finally at 165 minutes, the membrane bypass was closed off and the gas flow was directed through the high-pressure side of supported liquid membrane test cell. The figure shows that after exposure to the membrane, the relative humidity decreased rapidly and reached a value of 5% at 96 minutes and eventually stabilized at approximately 2.5 to 3% for the duration of the test. The figure shows that the $CO_2$ concentration also dropped rapidly after the flow was exposed to the membrane. Over this range, the decrease in $CO_2$ concentration was relatively linear and reached a value of 0.63% at a time of 349 minutes. The slope of the $CO_2$ concentration vs time was used to calculate a permeance of 1.0 E-4 scc/($cm^2$ s cm Hg).

FIG. 17 shows the total pressure as a function of time. The figure shows that before the loop was exposed to the membrane, the system was charged with our calibration gas (2.5 mol % $CO_2$, balance $O_2$) to a pressure of 0.4 atm. Pure 02 was then added to bring the system pressure up to just over 0.8 atm (atmospheric pressure at our facility in Golden Colo.), thereby reducing the $CO_2$ concentration to approximately 1.25 mol %. The system pressure was then reduced to 0.4 atm. This sequence was used to drop the $CO_2$ concentration to the desired value of 3.8 mm Hg. The pressure remained constant until the loop was opened to the membrane and then the figure shows that the pressure dropped at a relatively constant rate and reached a value of 0.37 atm at the end of the test. The pressure decrease shown here was the result of three factors: constant removal of gas for GC sampling, loss of water vapor through the membrane, and CO2 and O2 permeance through the membrane.

As mentioned in the test procedures, the losses were correct for due to $CO_2$, GC sampling, and water vapor loss and arrived at a $O_2$ permeance of 7E-7 scc/($cm^2$ s cm Hg). Compared to the $CO_2$ permeance, a $CO_2/O_2$ selectivity of 150 was obtained, a significant increase from the values obtained with the AP-Mim with the original anion.

Although the previous results obtained were very positive encouraging, the $O_2$ permeance was low enough that the change in pressure from GC sampling was causing significant uncertainty in the calculation of $O_2$ permeance. Therefore, to achieve better accuracy in our $O_2$ permeance calculations, the testing procedure was modified slightly in subsequent runs. Rather than operating the GC sampling pump continually, a test was conducted in which the pump was only operated for three short periods during the test: right before the syringe pump is started to obtain initial $CO_2$ after charging the reservoir with $CO_2$, just before the loop is open to the membrane and finally once at the end of the test after the membrane is isolated from the circulating flow. The data in FIG. 16 show that the change in $CO_2$ concentration is linear so using values at the start and end of the test will result in the same value as continual GC measurements. Moreover, this reduces the uncertainty in the $O_2$ permeance value by greatly reducing the pressure loss due to GC sampling.

Figure 18:
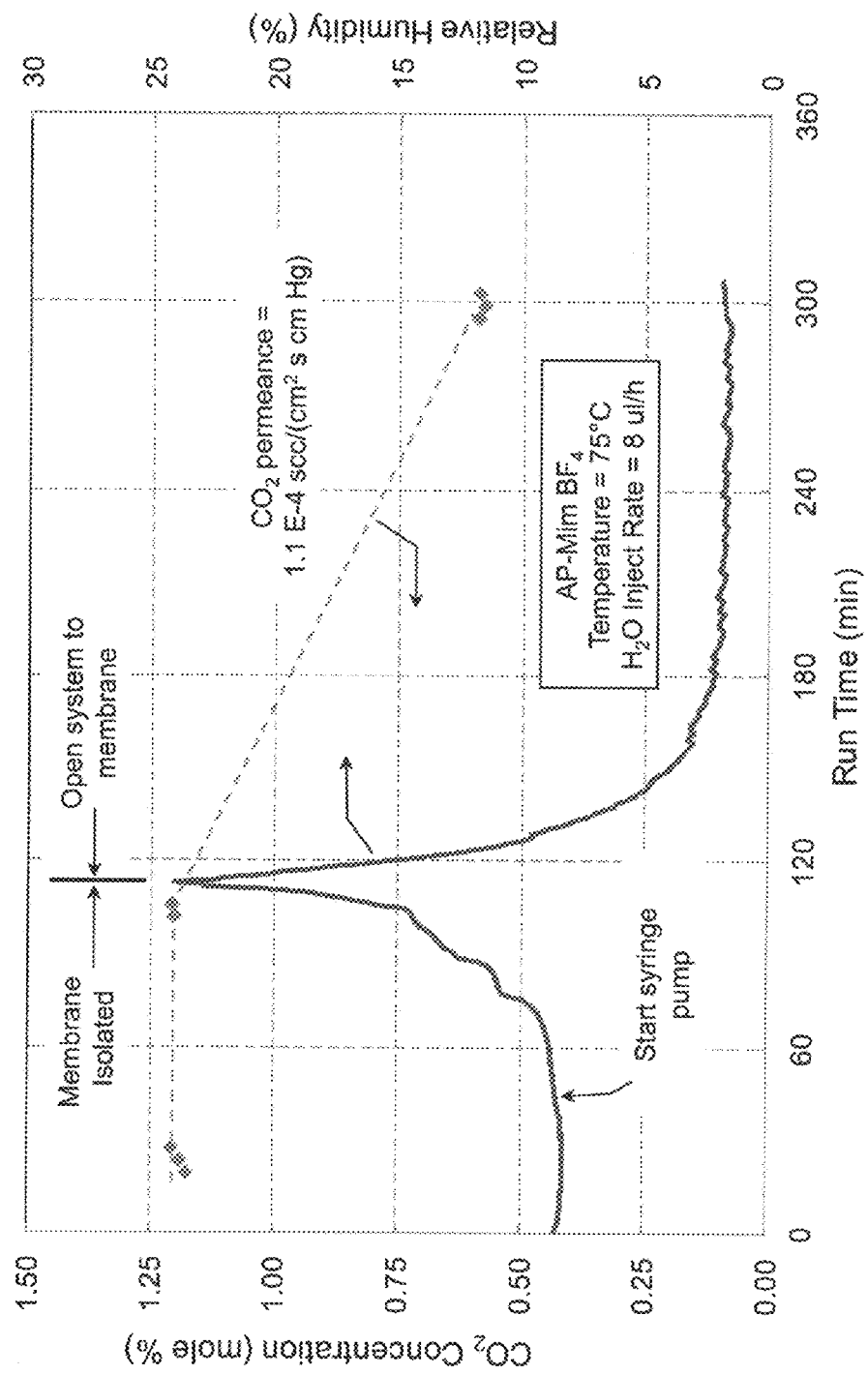
FIG. 18 illustrates $CO_2$ concentration and moisture as a function of time with the AP-Mim $BF_4$ at 75° C.
Figure 19:
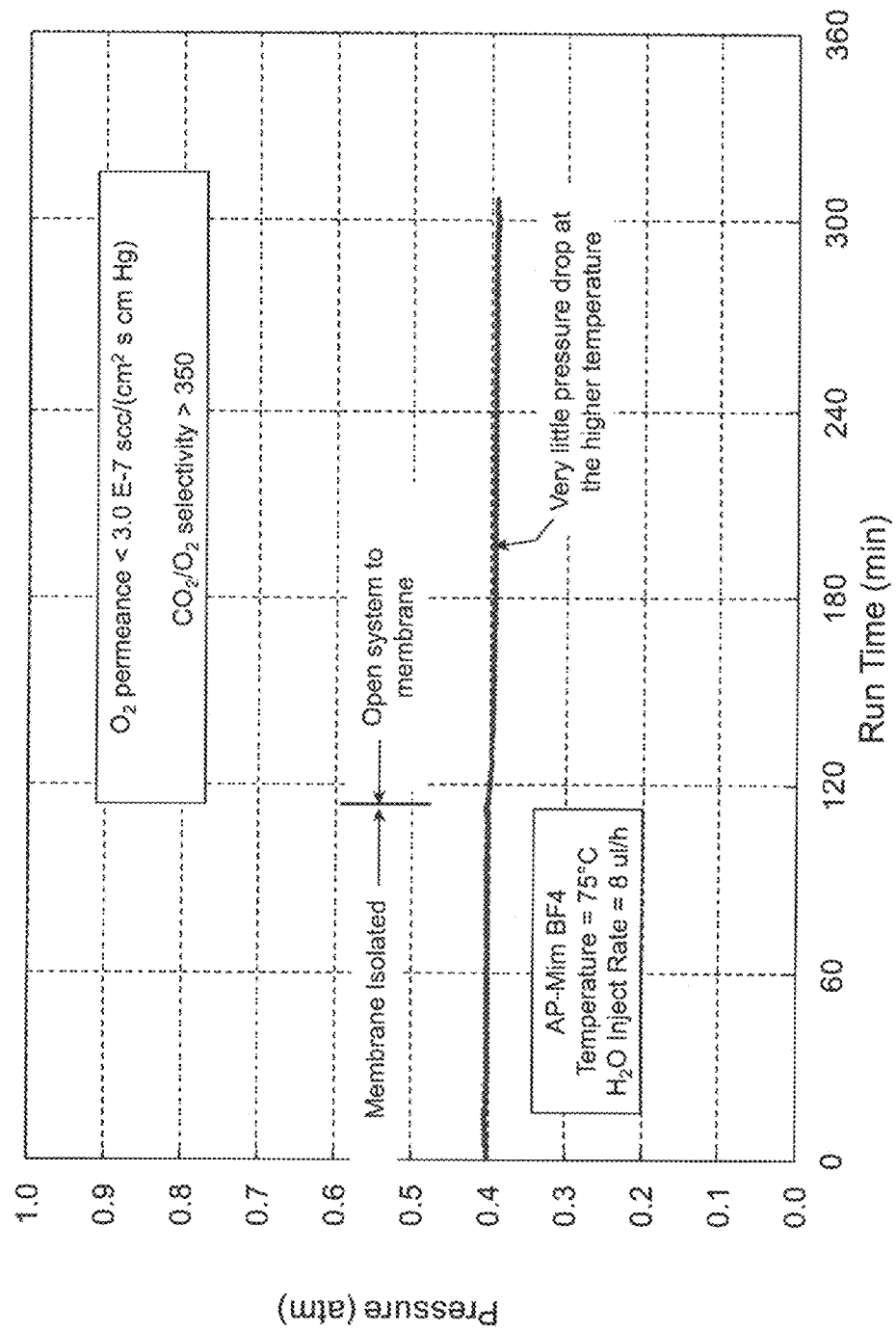
FIG. 19 illustrates Total pressure as a function of time with the AP-Mim $BF_4$ at 75° C.

The results of the test run with the revised procedure are included in FIG. 18 and FIG. 19. FIG. 18 shows that the moisture dropped rapidly when the circulating gas was exposed to the membrane and again reaches a steady state concentration of about 2 to 3%. In addition the figure shows that the $CO_2$ concentration dropped from 1.21 to 0.58% over the duration of the run, resulting in a permeance of 1.1E-4 scc/(cm2 s cm Hg). This value is approximately twice as high as the value obtained in the previous figure and demonstrates that temperature has a strong effect on the rate of CO2 removal in this system.

FIG. 19 shows the total pressure obtained during the test. In this case, the magnitude of the pressure drop was much lower than in the previous test, reflecting the pressure loss by the continuous operation of the GC sampling pump. In this case, there was very little pressure drop after the loop was exposed to the membrane. Once again immediately after the loop was opened to the membrane there was a noticeable pressure drop, which was due primarily to the loss of water vapor, as shown in FIG. 18. However after that change, the pressure remained very constant. For example, FIG. 19 shows that the pressure was 0.3949 atm at 180 minutes; however at 300 minutes or two hours later the pressure had only dropped to 0.3929 atm. This difference is very small and is right at the resolution of our pressure transducer. Therefore, it is estimated that the permeance obtained during this run was <3E-7 scc/($cm^2$ s cm Hg). Combining this value with the $CO_2$ permeance reported above, results in a $CO_2/O_2$ selectivity of >350.

The results presented in FIG. 18 and FIG. 19 are very positive and demonstrate that the required value was reached for permeance and are also approaching the $CO_2/O_2$ selectivity target. Although a selectivity of >350 is encouraging, the $O_2$ permeance was less than our detection limit in this test rig. Therefore, the $O_2$ permeance test was repeated in the single-gas test rig, which for $O_2$ permeance has a lower detection limit than the mixed gas test rig.

Figure 20:
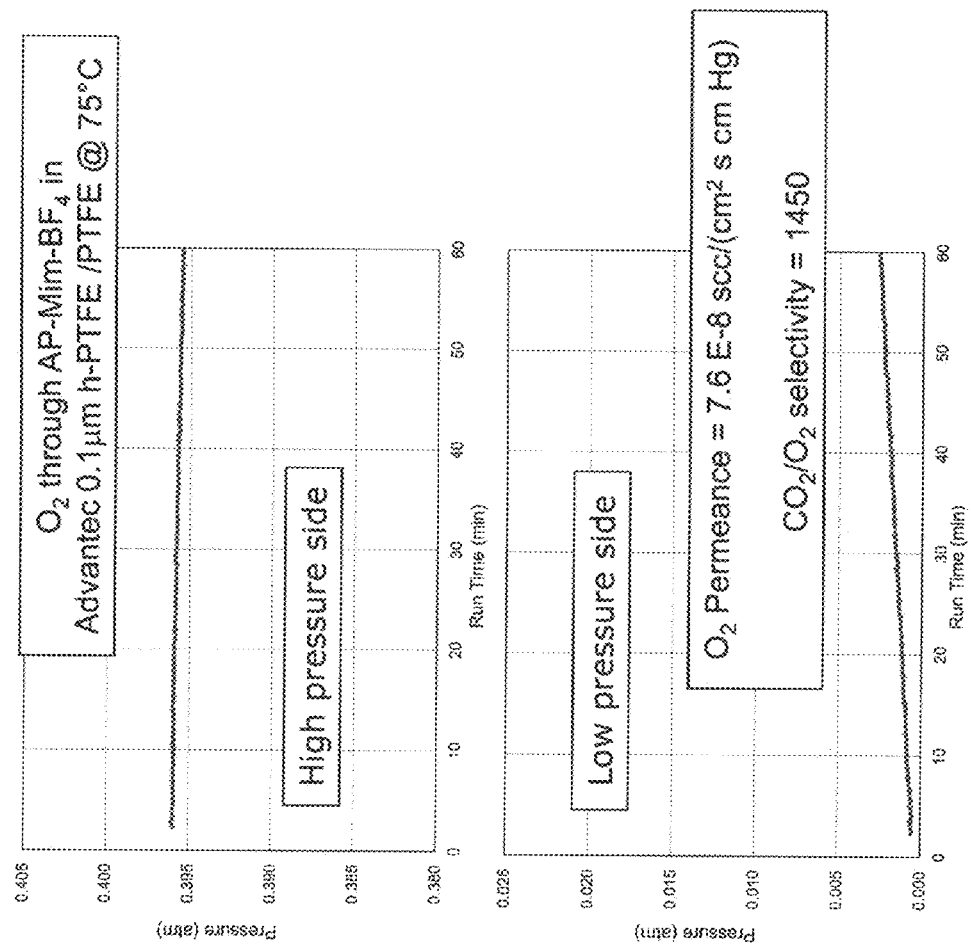
FIG. 20 illustrates $O_2$ permeation results obtained for AP-Mim $BF_4$ in the h-PTFE/PTFE layered membrane at 75° C.

The results of the single gas tests for $O_2$ with the modified AP-Mim are shown in FIG. 20. The figure shows that the pressure in the upper reservoir decreased from 0.3960 atm to 0.3955 atm over a period of 50 minutes. Likewise, the pressure in the lower reservoir, which has only ⅙ the volume of the large reservoir, increased from 0.002 atm to 0.004 atm over the same time period. Using the data in the figure, an $O_2$ permeance of 7.6E-8 scc/(cm2 s cm Hg) was obtained. Using this value along with the $CO_2$ permeance reported in FIG. 18, it was calculated that $CO_2/O_2$ selectivity of this ionic liquid at a temperature of 75° C. is 1450. This value is greater than our initial target value of 1300 and therefore these results show that the target $CO_2$ permeation and $CO_2/O_2$ selectivity requirements established were obtained. These are very positive results and demonstrate the potential feasibility of using a supported liquid membrane for $CO_2$ control.

Fabrication of a Module Containing Layered Hollow Fibers

As pointed out above, in order to meet the volume requirements for a $CO_2$ control system in the PLSS, the SLM membrane must be incorporated into a hollow fiber form and this is the purpose of this task. Moreover, because of the achievement of promising results in the flat sheet configuration with a two layered membrane system, the hollow fibers should have a similar structure. In the flat sheet configuration, the ionic liquid is contained in an open pore hydrophilic membrane on the high-pressure side, while a hydrophobic membrane on the low pressure side keeps the liquid from being forced out the membrane. Therefore, in order to achieve the same performance in the hollow fiber form, our original focus was to identify a similar, commercially available layered material where the functionalized ionic liquid would be contained in the inside of the hollow fiber wall and a hydrophobic outer shell on the low pressure side would prevent the IL from being forced out of the fibers.

Figure 21:
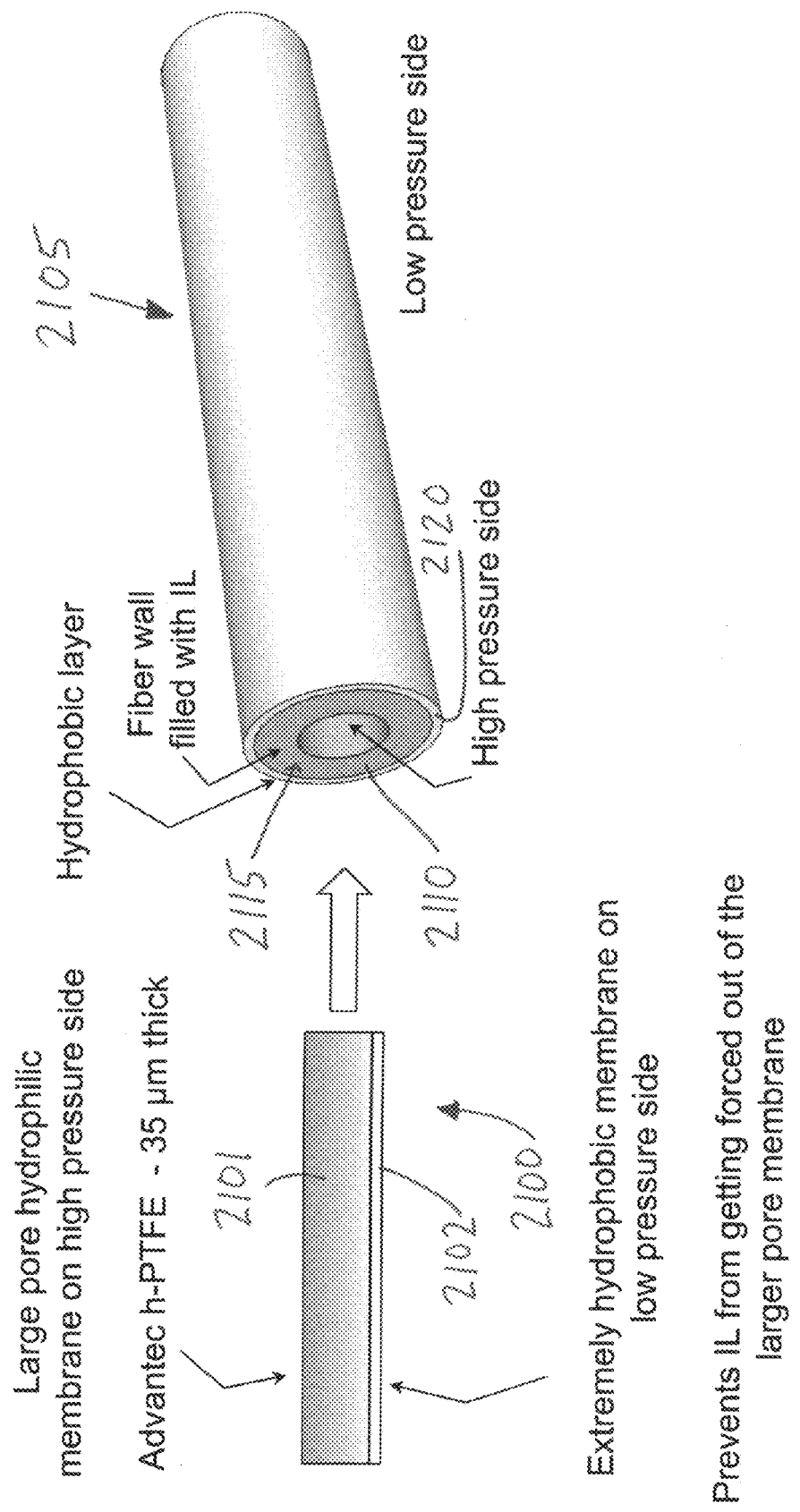
FIG. 21 illustrates an exemplary embodiment of a two layer flat sheet h-PTFE/PTFE I membrane (left side) and the analogous two layer form in a hollow fiber (right side)

FIG. 21 illustrates the layered membrane in both the flat sheet 2100 and hollow fiber 2105 configurations. The flat sheet 2100 (left side) shows the layered membrane that produced the very promising results described above. The top layer 2101 is a hydrophilic PTFE membrane that is 35 µm thick, has an average pore size of 0.1 µm and contains the IL. However, if this membrane were used by itself, the differential pressure of 0.4 atm would force the IL out of the membrane pores. To prevent that from occurring, the thin, hydrophobic membrane 2102 is placed on the low-pressure side. Since it is very hydrophobic, the ionic liquid will not be forced into its pores.

On the right side, the analogous configuration is shown in a hollow fiber form 2105. The inside of the fiber wall 2110 contains the ionic liquid 2115, while a thin, hydrophobic layer 2120 on the outside of the wall prevents the liquid from being forced out to the shell side of the membrane. In this configuration, the process flow is directed through the center of the hollow fiber (or lumen) while the shell side is exposed to vacuum. Thus, as the $CO_2$ contained in the process flow is directed through the fiber, it is absorbed by the functionalized ionic liquid in the wall and then diffuses to the outside of the fiber where it desorbs into the vacuum.

Unfortunately, a commercial source of fibers was not identified that had such a configuration. Therefore, a method was created to fabricate the layered structure within existing hollow fibers. There are two parts to this process. First, the fibers have to be potted into a module that can direct a gas or liquid flow through the lumen of a group of fibers, while exposing the outside of the fibers to a separate environment. Then the process identified to generate the layered structure can be performed. In the following sections, there is summarized the method developed to fabricate hollow fiber modules using commercially procured hollow fibers and then describe the interfacial polymerization process identified that should allow generation the layered hollow fiber and simulate the very promising flat sheet performance described earlier.

Hollow Fiber Fabrication

A series of more modules was fabricated in order to develop and optimize the polymerization process. These modules are 5½-in long and ⅜-in in diameter at the tube. Each module contains a 2⅞-in width of the fiber mat, with fibers that are 6¼-in long. However, about 1-in of the fiber length on each end is enclosed in urethane leaving an effective fiber length of 4⅛-in, resulting in an overall surface area of 110 cm². After the potting process was complete and the urethane had set, tests were carried out with water to verify the integrity of the seal around the edge of the fibers and inner wall of the module housing using water pressure.

Interfacial Polymerization of the Hollow Fiber

Figure 22:
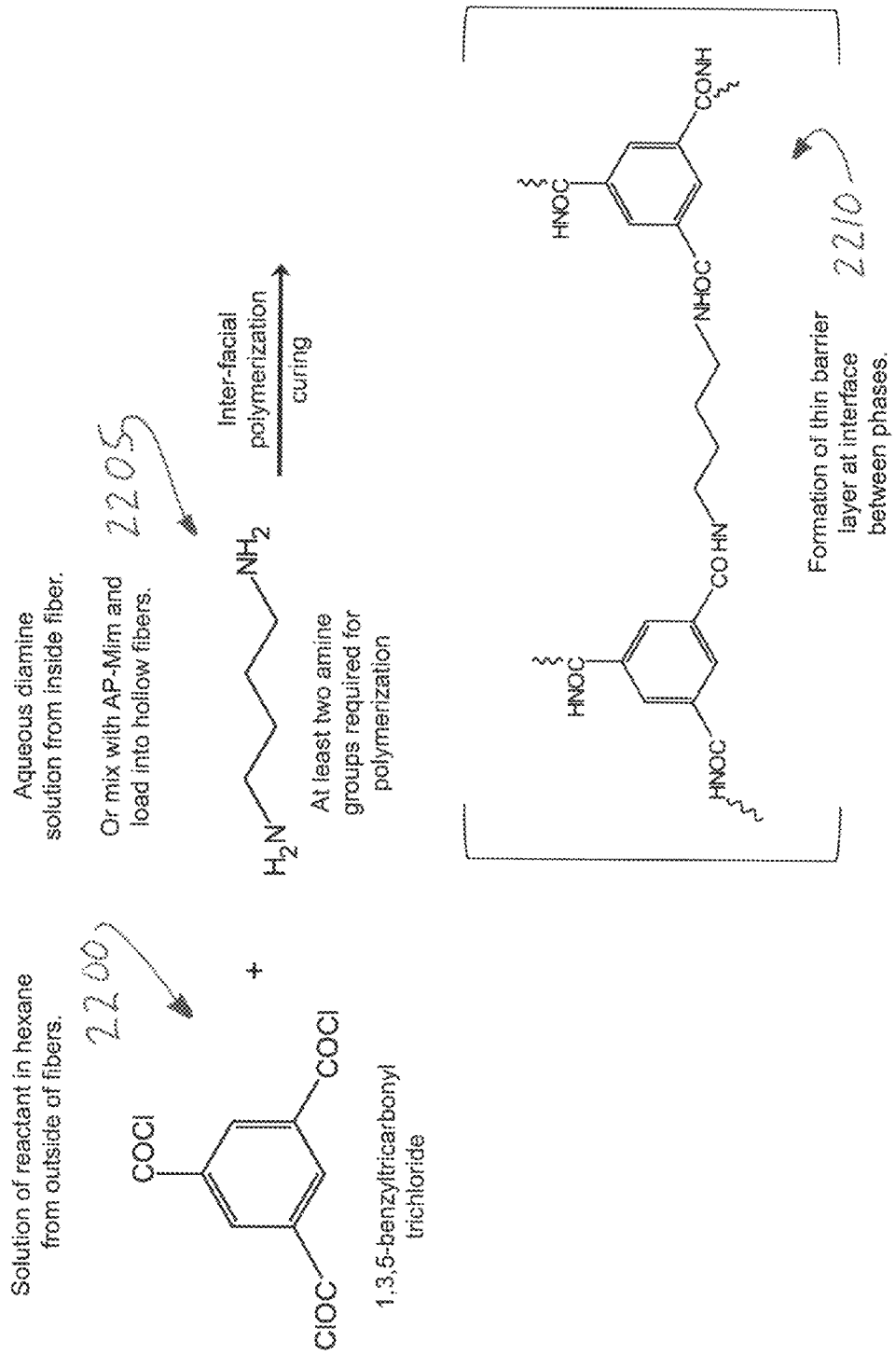
FIG. 22 illustrates a polymerization reaction between an acid chloride and a diamine.

Since a commercial source of layered fibers was not identified, a method was identified to add the polymer layer to the outside of the fiber and generate a layered structure in-situ (Morgan, P. W. and S. Kwolek (1996). "Interfacial Polycondensation. II. Fundamentals of Polymer Formation at Liquid Interfaces, Journal of Polymer Science: Part A: Polymer Chemistry, 34, pg. 531-559.) The process is based on the polymerization reaction that occurs between an acid chloride and a compound containing at least two primary amine groups. An example of such a reaction is shown in FIG. 22. In this case, 1,3,5-benzyltricarbonyl trichloride 2200 reacts with butyldiamine 2205 and generates a polyamide 2210. The 1,3,5-benzyltricarbonyl is contained in an organic phase such as hexane while the diamine is contained in an aqueous phase. These solutions are not miscible and thus when they are brought into contact, the reaction can only occur at the interface between the solutions.

Figure 23:
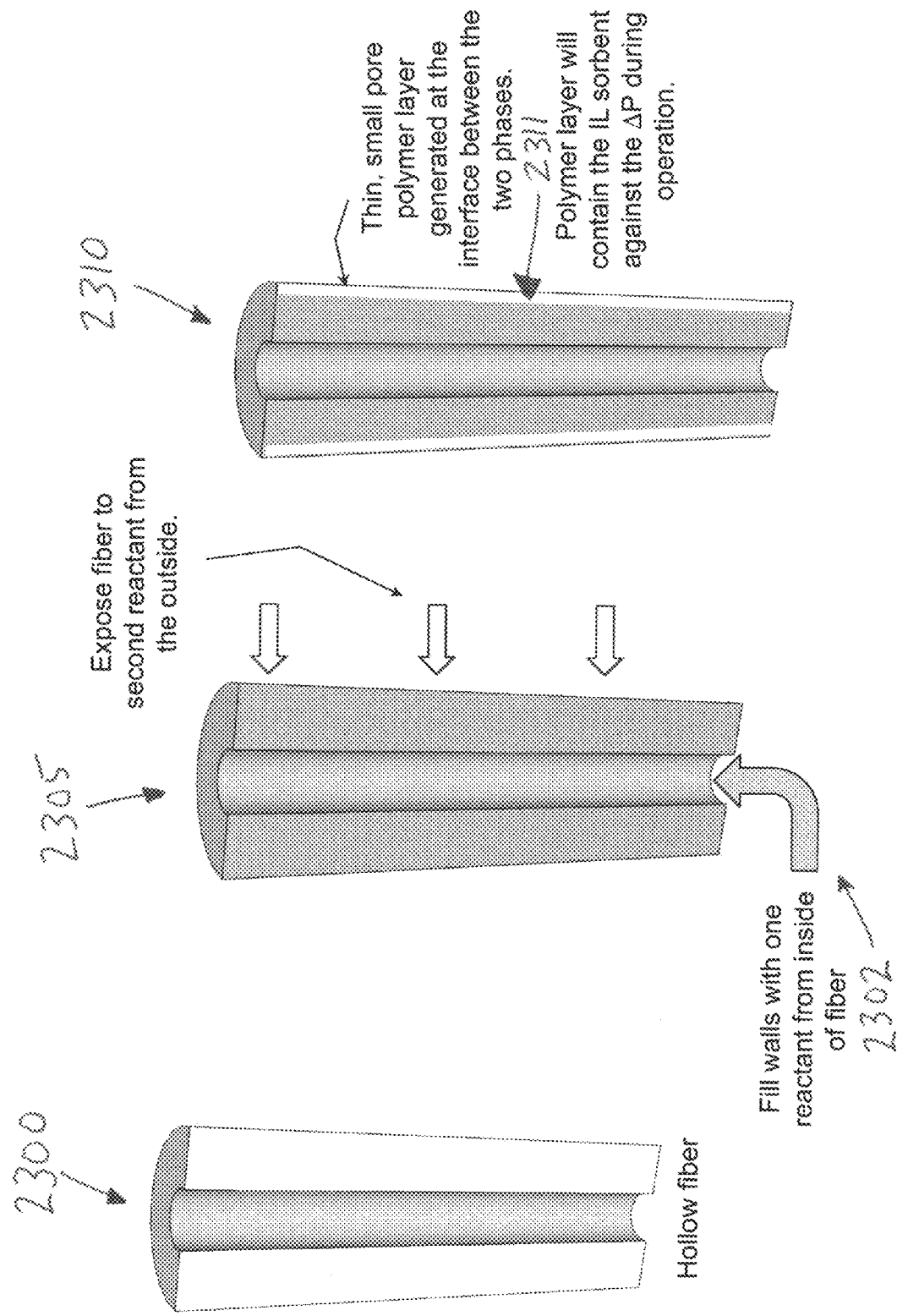
FIG. 23 illustrates an exemplary method to add a polymer layer on the shell side using interfacial polymerization.

The method to incorporate the polymer into the hollow fiber is illustrated FIG. 23. The figure on the left shows a cross section of an empty hollow fiber 2300. First, the aqueous solution containing the butyldiamine 2301 was flowed through the shell side of the module. The fibers are not easily wetted with water so this solution will not penetrate into the wall of the fiber. Once the shell side was filled, the hexane solution was flowed containing the 1,3,5-benzyltricarbonyl trichloride through the inside of the fibers. These fibers are easily wetted by organic solutions such as hexane and therefore the solution will fill the fibers with reactant 2302 (center illustration 2305). However, the two solutions will contact each other at the outside edge of the fiber, and as illustrated by the diagram 2310 in the right side of FIG. 23, a polymer layer 2311 will form at that location. Moreover, Morgan and Kwolek (1996) show that the polymer layer tends to grow into the organic side so it will be formed inside the polymer layer but at the outside edge as shown in the figure.

The interfacial polymerization process was carried out on one of the modules. The reacting solutions were prepared by dissolving 5.3 grams of 1,3,5-benzyltricarbonyl trichloride in 100 ml of n-hexane and 4.93 grams of butyl diamine in 100 ml of water. A single head peristaltic pump was used to flow both solutions through the module. The line containing the aqueous amine solution was connected to the shell side of the module and pumped approximately 60 mls of solution through this path. The line was clamped and removed from the peristaltic pump. The acid chloride hexane solution was then connected to the lumen ports (going through the inside of the pores) and flowed 60 ml of solution through the module from bottom to top assuring that the inside flow path was filled and the fibers were completely wetted so the hexane solution was in contact with the aqueous amine solution at the outer edge of the hollow fiber. The solutions were left in contact for one minute and then flushed the shell side with 100 ml of water and drained the water out of the shell. At this point, the hexane solution was drained out of the hollow fiber side. The module was then placed in a vacuum oven at 40° C. for four hours to remove the solvents.

In order to evaluate the effect of the polymerization process, $N_2$ permeation tests were carried on the module after it was prepared and after the polymerization process had been performed. The module was installed in a single gas test rig and the same process was used as in the past to evaluate the performance of the module.

Figure 24:
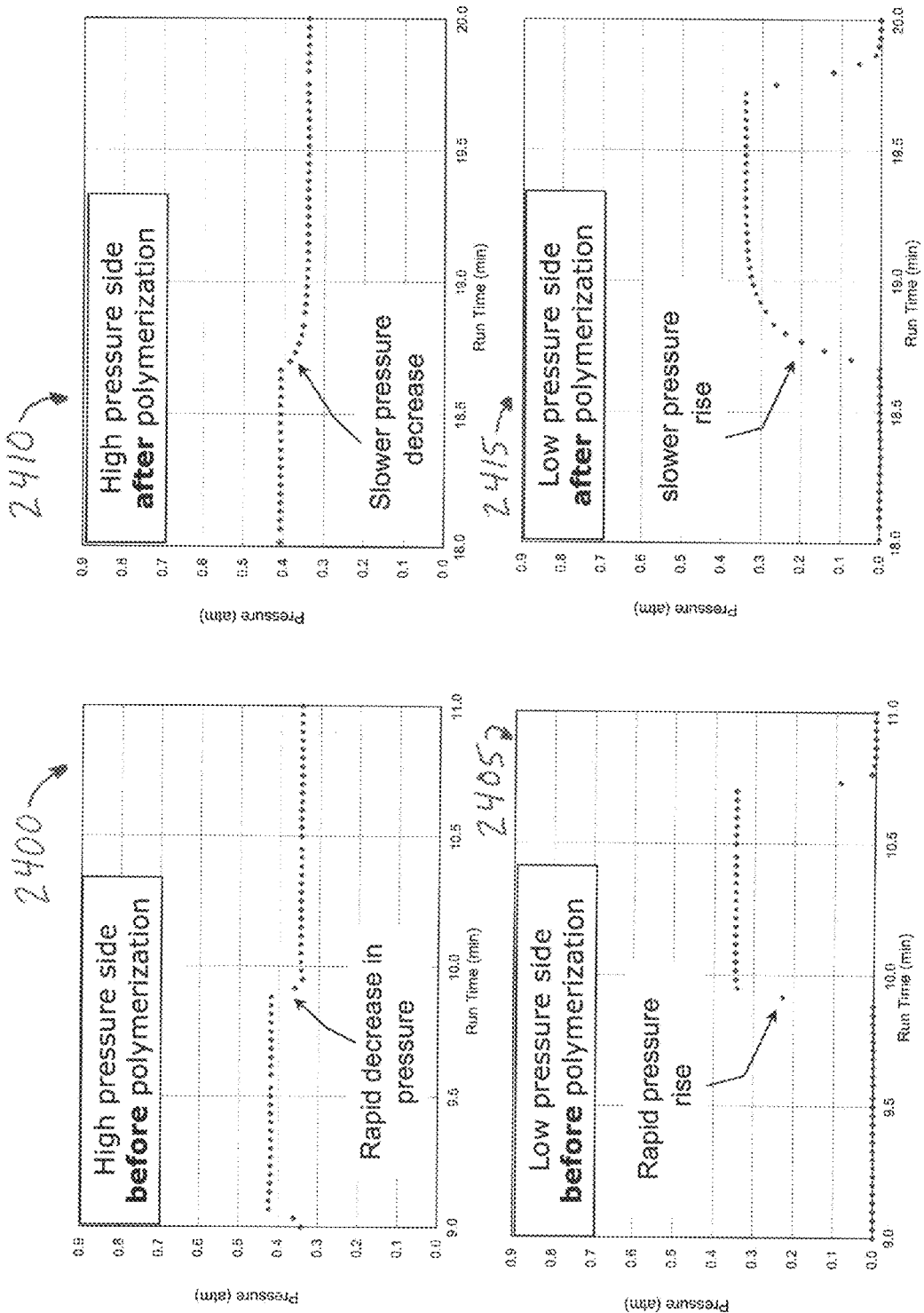
FIG. 24 illustrates $N_2$ permeation results with a hollow fiber module: before polymerization (left side) and after polymerization (right side).

Permeation test data obtained on the same module before the polymerization process 2400, 2405 are shown on the left side of FIG. 24 while the data obtained after the polymerization process 2410, 2415 are shown on the right side of the figure. The data clearly show that the polymerization process has decreased the permeation rate of the fibers. Before the polymerization step was carried out, the figures on the left side 2400, 2405 show that the pressure changes were very rapid. On the high pressure side, the top FIG. 2410 shows that the pressure dropped from 0.42 atm to 0.35 atm 0.1 min or six seconds. In addition, on the low-pressure side the figure on the bottom 2405 shows that the pressure increased from <0.01 atm to 0.35 atm in a similar amount of time. On the other hand, when the polymer was added to the hollow fiber the figures on the right side of the figure show that the pressure changes were much slower. On the high-pressure side, the pressure drop began at 18.7 minutes but the pressure did not become stable at 0.35 atm until 19.1 minutes. The results on the low pressure show similar results and the gradual change in slope is readily apparent in this figure. Thus, in this case 0.4 minutes or 24 seconds were required to reach steady state with the polymer compared to about 4 seconds before the polymer was added.

Permeance was calculated using the same procedures used in the past. Before the polymer was added, an $N_2$ permeance of 7.82E-3 scc/(cm$^2$ s cm Hg) was obtained. This value is relatively close to the manufacturer's specification of 1.67E-2 scc/(cm$^2$ s cm Hg) and indicates that that module has been potted in the housing in a way that exposes the expected surface area of the fibers to vacuum on the shell side and process pressure on the lumen side.

After the polymer was added, a permeance of 2.21E-3 scc/(cm$^2$ s cm Hg) was obtained, which is significantly lower than the value obtained for the untreated hollow fiber. This shows that at least a substantial portion of the fiber surface was coated with the polymer, which was our objective.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A portable life support system for removal of at least one selected gas, the system comprising:
 a supported liquid membrane having a first side and a second side in opposition to one another, the first side configured for disposition toward an astronaut and the second side configured for disposition toward a vacuum atmosphere; and
 an ionic liquid disposed between the first side and the second side of the supported liquid membrane, the ionic liquid configured for removal of at least one selected gas from a region housing the astronaut adjacent the first side of the supported liquid membrane to the vacuum atmosphere adjacent the second side of the supported liquid membrane, the second side of the supported liquid membrane having a hydrophobic layer so as to prevent removal of the ionic liquid into the vacuum atmosphere, wherein the supported liquid membrane is configured to provide a higher affinity between carbon dioxide and the ionic liquid than a remainder of components of exhaled air, and wherein the supported liquid membrane has a selectivity for carbon dioxide over oxygen;
 wherein the ionic liquid includes a functionalized amine group as the cation and at least one anion including tetrafluoroborate ($BF_4^-$); and
 wherein the primary amine functionalized cation is 1-(3-aminopropyl)-3-methylimidazolium (AP-Mim$^+$).

2. The system of claim 1, wherein the at least one selected gas is carbon dioxide.

3. The system of claim 2, wherein the supported liquid membrane with the ionic liquid is configured to control the region housing the astronaut to reduce an amount of carbon dioxide exposed to the astronaut.

4. The system of claim 2, wherein the supported liquid membrane with the ionic liquid is selective for carbon dioxide over oxygen and nitrogen.

5. The system of claim 2, wherein the supported liquid membrane with the ionic liquid is a continuous system for carbon dioxide removal.

6. The system of claim 2, wherein the supported liquid membrane with the ionic liquid is configured to provide a permeation rate of carbon dioxide based on size and weight limitations for an astronaut.

7. The system of claim 1, wherein the at least one selected gas is water vapor.

8. The system of claim 1, wherein the supported liquid membrane with the ionic liquid is configured to control the region housing the astronaut to reduce an amount of water vapor exposed to the astronaut.

9. The system of claim 1, wherein the supported liquid membrane with the ionic liquid is a continuous system for water vapor removal.

10. The system of claim 1, wherein the at least one selected gas includes carbon dioxide and water vapor, wherein the component is configured for simultaneous removal of the carbon dioxide and the water vapor.

11. The system of claim 1, wherein the supported liquid membrane with the ionic liquid is regenerable by exposure to the vacuum without a temperature change to the supported liquid membrane.

12. The system of claim 1, wherein the supported liquid membrane with the ionic liquid has a zero vapor pressure, wherein the ionic liquid is prevented from evaporating to the vacuum.

13. The system of claim 1, wherein the ionic liquid includes a functionalized amine group as the cation.

14. The system of claim 1, wherein the ionic liquid cation includes a primary amine.

15. The system of claim 1, wherein the ionic liquid cation includes a secondary amine.

16. The system of claim 1, wherein the ionic liquid cation includes a tertiary amine.

17. The system of claim 16, wherein the tertiary amine functionalized cation is 1-butyl-4-(N,N-dimethylamino)pyridinium (B-DMAPyr$^+$).

18. The system of claim 1, wherein the supported liquid membrane is a hollow fiber form with an inside surface and an outside surface, the inside surface of the hollow fiber providing a first side and the outside surface of the hollow fiber providing a second side.

19. The system of claim 1, wherein the portable life support system is a space suit.

20. The system of claim 1, wherein the selectivity for carbon dioxide over oxygen is at least a threshold amount of 500.

21. The system of claim 1, wherein the selectivity for carbon dioxide over oxygen is at least a threshold amount of 1300.

* * * * *